(12) United States Patent
Paulus

(10) Patent No.: US 11,504,415 B2
(45) Date of Patent: Nov. 22, 2022

(54) TREATMENT OF HEART FAILURE WITH PRESERVED EJECTION FRACTION

(71) Applicant: Stichting VUmc, Amsterdam (NL)

(72) Inventor: Walter Joseph Paulus, Meise (BE)

(73) Assignee: STICHTING VUMC, Amsterdam (NL)

( * ) Notice: Subject to any disclaimer, the term of this patent is extended or adjusted under 35 U.S.C. 154(b) by 0 days.

(21) Appl. No.: 16/095,273

(22) PCT Filed: Apr. 21, 2017

(86) PCT No.: PCT/NL2017/050254
§ 371 (c)(1),
(2) Date: Oct. 19, 2018

(87) PCT Pub. No.: WO2017/183978
PCT Pub. Date: Oct. 26, 2017

(65) Prior Publication Data
US 2019/0160147 A1    May 30, 2019

(30) Foreign Application Priority Data
Apr. 21, 2016 (EP) .................................. 16166468

(51) Int. Cl.
*A61K 38/17*    (2006.01)
*A61K 31/121*   (2006.01)

(52) U.S. Cl.
CPC ........ *A61K 38/1761* (2013.01); *A61K 31/121* (2013.01); *A61K 38/17* (2013.01)

(58) Field of Classification Search
None
See application file for complete search history.

(56) References Cited

U.S. PATENT DOCUMENTS 4,169,157 A    9/1979  Kijima et al.
2003/0134907 A1 *  7/2003  Takahashi ............... A61K 31/12
                                                        514/675

FOREIGN PATENT DOCUMENTS

WO    WO 2008/013985    *  1/2008  ........... A61K 31/395
WO        2017/183978 A1    10/2017

OTHER PUBLICATIONS

Vos et al., Biochimica et Biophysica Acta 1793 (2009) 1343-1353 (Year: 2009).*
Bhattacharya et al., PLoS ONE 12(3): e0171355. https://doi.org/10.1371/journal.pone.0171355; 22 pages total (Year: 2017).*
Jafarlou et al., Journal of Biological Regulators & Homeostatic Agents, 2016: 30: 315-321 (Year: 2016).*
Marunouchi et al. (European Journal of Pharmacology 730 (2014) 140-147 (Year: 2014).*
Van Marion et al., Heart Rhythm 2020;17: 115-122 (Year: 2020).*
Gazewood et al., Am Fam Physician. 2017; 96(9): 582-588 (Year: 2017).*
Borlaug and Paulus, European Heart Journal (2011) 32, 670-679 (Year: 2011).*
Yoon et al., J Cardiovasc Ultrasound. Sep. 2015; 23(3): 150-157 (Year: 2015).*
De Keulenaerand Brutsaert, Progress in Cardiovascular Diseases, vol. 49, No. 4 (Jan./ Feb.), 2007: pp. 275-283 (Year: 2007).*
Bshiebish et al., J Saudi Heart Assoc. 2019; 31:100-105 (Year: 2019).*
Borlaug and Redfield, Circulation. 2011; 123: 2006-2014 (Year: 2011).*
Bhattacharya et al., PLoS ONE 12(3): e0171355. https://doi.org/10.1371/journal.pone.0171355 (Year: 2017).*
Fenton et al., Medicinal Chemistry Research (2020) 29:1133-1146 (Year: 2020).*
Sanbe et al., PLoS ONE 4(4): e5351. doi:10.1371/journal.pone.0005351 (Year: 2009).*
Aoki et al., Circ J 2011; 75: 2605-2613 (Year: 2011).*
Zhang et al., Science advances, (20190500) vol. 5, No. 5, pp. eaaw 5870 (Year: 2019).*
Franssen et al., Circ Heart Fail. 2017;10:e003626. DOI: 10.1161/CIRCHEARTFAILURE.116.003626 (Year: 2017).*
Pinz et al., Unmasking different mechanical and energetic roles for the small heat shock proteins CryAB and HSPB2 using genetically modified mouse hearts, The FASEB Journal, Aug. 28, 2007, pp. 84-92, vol. 22, No. 1.
Marunouchi et al., Protective effect of geranylgeranylacetone via enhanced induction of HSPB1 and HSPB8 in mitochondria of the failing heart following myocardial infarction in rats, European Journal of Pharmacology, Apr. 11, 2014, pp. 140-147, vol. 730.
Kumarapeli et al., Protein quality control in protection against systolic overload cardiomyopathy the long term role of small heat shock proteins. Am J Transl Res, Jul. 21, 2010, pp. 390-401, vol. 2.
Golenhofen et al., Ischemia-induced increase of stiffness of [alpha]B-crystallin/HSPB2-deficient myocardium, Pflugers Archiv—European Journal of Physiology, Springer, Berlin, Germany, Jan. 1, 2006, pp. 518-525, vol. 451, No. 4.

(Continued)

*Primary Examiner* — Christina M Borgeest
(74) *Attorney, Agent, or Firm* — TraskBritt

(57) ABSTRACT

The treatment of diastolic dysfunction in a subject and, in particular, compositions for use and methods in treating diastolic dysfunction are disclosed. In one aspect, the disclosure provides a composition for use comprising a therapeutically effective amount of a substance that increases the level and/or activity of a crystalline protein in cardiomyocytes of the subject. In particular, the composition for use according to the disclosure comprises a therapeutically effective amount of the alpha B crystalline protein. It was found that the composition for use is capable of treating diastolic dysfunction and diastolic heart disease in subjects with failing hearts that have a higher cardiomyocyte stiffness than controls. Particularly, addition of alpha B crystalline reduced the higher stiffness of failing cardiomyocytes to the level observed in control cardiomyocytes.

Figure 1A:
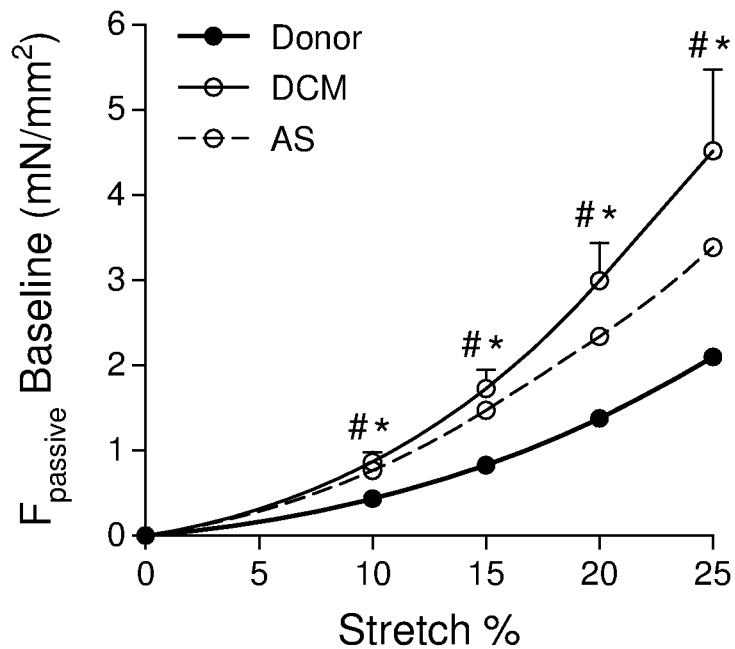

11 Claims, 11 Drawing Sheets
Specification includes a Sequence Listing.

(56) References Cited

OTHER PUBLICATIONS

Cha et al., Abstract 18503 Geranylgeranylacetone (gga) and Gga-derivatives Inhibit Acetylcholine-activated K+ Current In Mouse Atrial Cardiomyocyte; Possible Mechanism For Af Suppression, Circulation, Nov. 10, 2015, URLhttpcirc.ahajournals.orgcontent132Suppl_3A18503.shortrss=1&related-urls=yes&legid-circulationaha;132Suppl_3A18503, retrieved on Sep. 22, 2016.

PCT International Search Report, PCT/NL2017/050254, dated Sep. 8, 2017.

PCT International Written Opinion, PCT/NL2017/050254, dated Sep. 8, 2017.

Solomon et al. "Angiotensin-Neprilysin Inhibition in Heart Failure with Preserved Ejection Fraction" N Engl J Med 2019; 381:1609-20 DOI: 10.1056/NEJMoa1908655.

Borbély et al. "Cardiomyocyte stiffness in diastolic heart failure" Circulation. 2005; 111(6):774-81. doi:10.1161/01.CIR.0000155257.33485.6D.

Borbély et al. "Hypophosphorylation of the Stiff N2B titin isoform raises cardiomyocyte resting tension in failing human myocardium" Circ. Res. 2009; 104(6):780-6. doi:10.1161/CIRCRESAHA.108.193326.

Granzier et al. "Passive tension in cardiac muscle: contribution of collagen, titin, microtubules, and intermediate filaments" Biophys. J. 1995; 68(March):1027-1044. doi:10.1016/S0006-3495(95)80278-X.

Hamdani et al. "Myocardial titin hypophosphorylation importantly contributes to heart failure with preserved ejection fraction in a rat metabolic risk model" Circ. Heart Fail. 2013; 6(6):1239-49. doi:10.1161/CIRCHEARTFAILURE.113.000539.

Kötter et al. "Human myocytes are protected from titin aggregation-induced stiffening by small heat shock proteins" J. Cell. Biol. 2014; 204(2):187-202. doi:10.1083/jcb.201306077.

Roh et al. "Why Don't We Have Proven Treatments for HFpEF?" Circulation Research (Apr. 2017) 120:1243-1245.

Van Heerebeek et al. "Myocardial structure and function differ in systolic and diastolic heart failure" Circulation. 2006; 113(16):1966-73. doi:10.1161/CIRCULATIONAHA.105.587519.

Zile et al. "Myocardial Stiffness in Patients with Heart Failure and a Preserved Ejection Fraction: Contributions of Collagen and Titin" 2015. doi:10.1161/CIRCULATIONAHA.114.013215.

Røe et al. "Increased passive stiffness promotes diastolic dysfunction despite improved Ca21 handling during left ventricular concentric hypertrophy" May 2017, Cardiovascular Research 113, pp. 1161-1172.

Roh et al. "Why don't we have proven treatments for HFpEF?" Circulation Research 120(8) (Apr. 2017) pp. 1243-1245.

Expert's Declaration of Etto Christoph Eringa dated Apr. 13, 2022.

Waddingham et al. "Boosting small heat shock proteins lowers cardiomyocyte passive stiffness in experimental heart failure with preserved ejection fraction" (May 2018) Eur J Heart Failure. 20, p. 24.

* cited by examiner

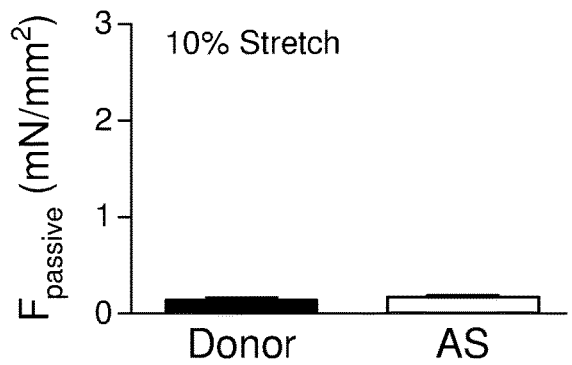
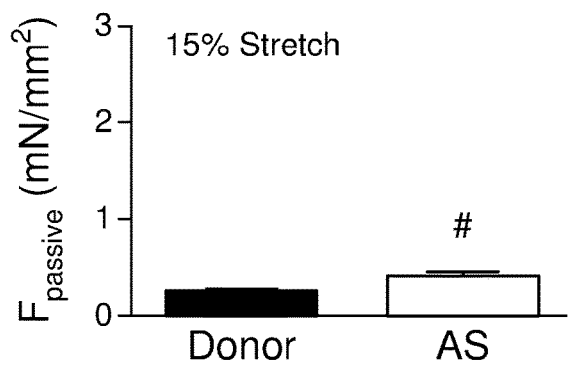
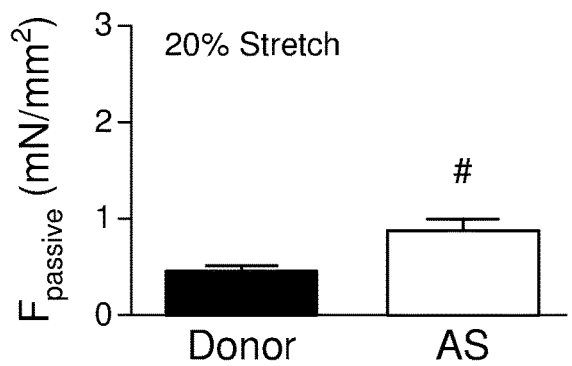
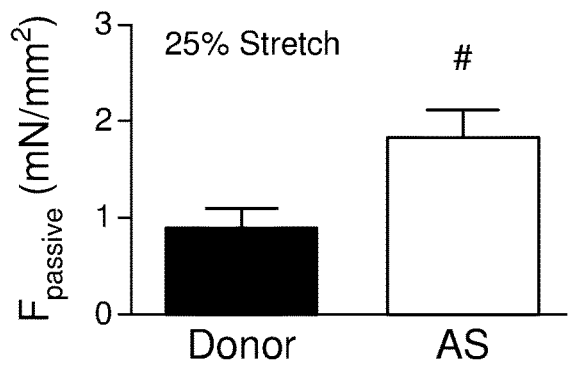
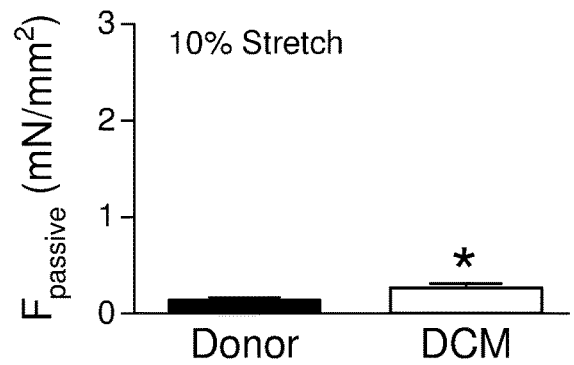
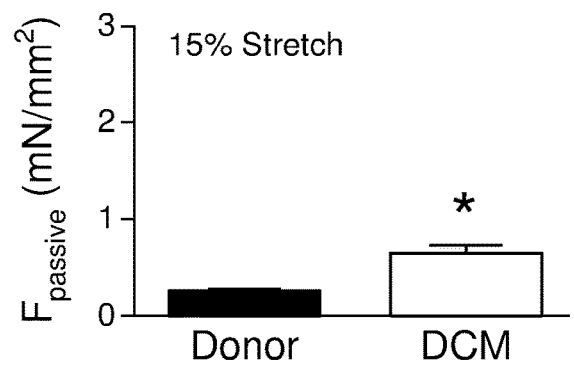
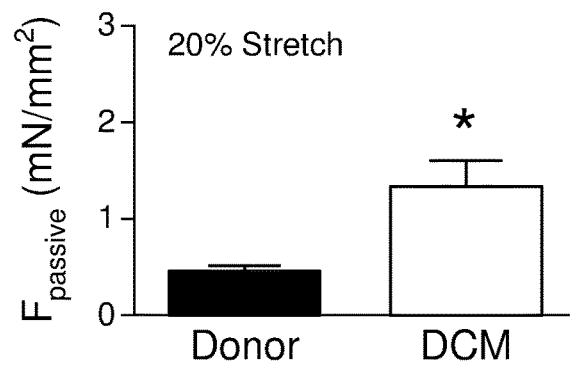
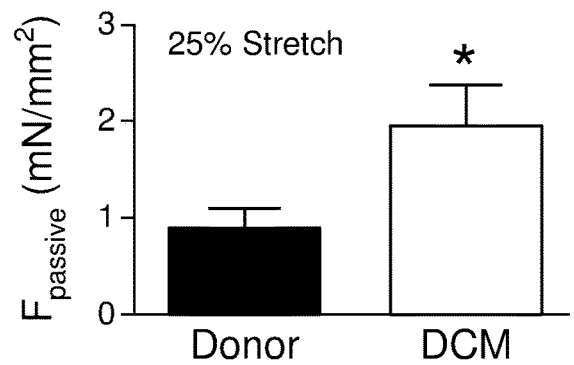
Fig. 2A
Fig. 2B

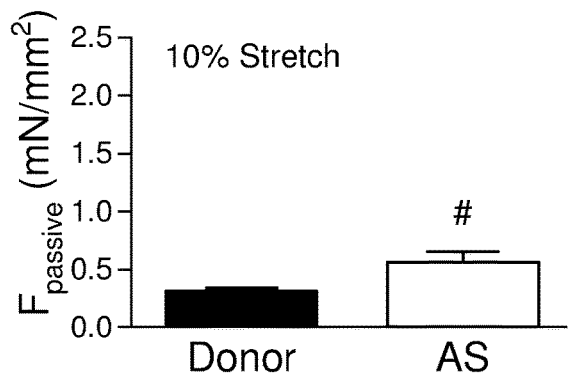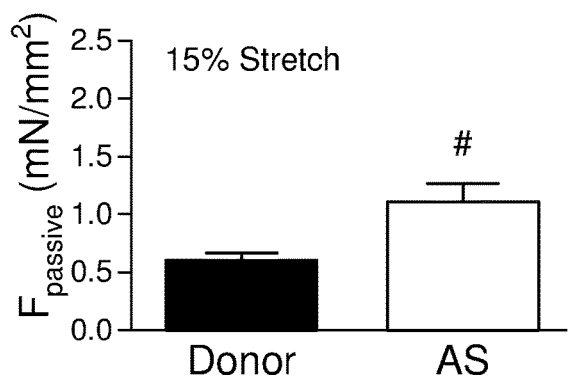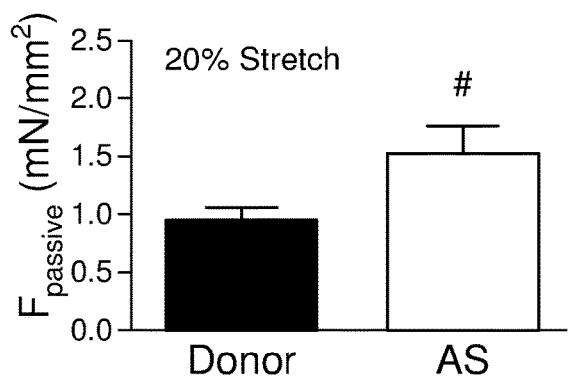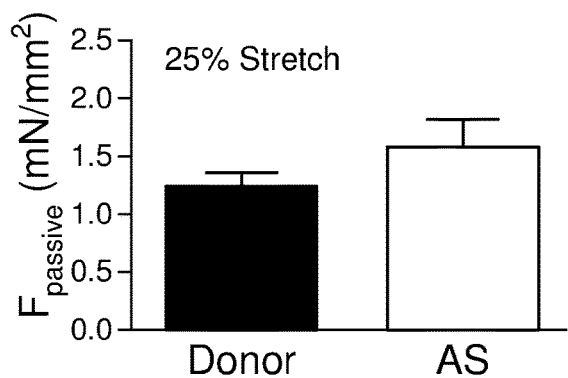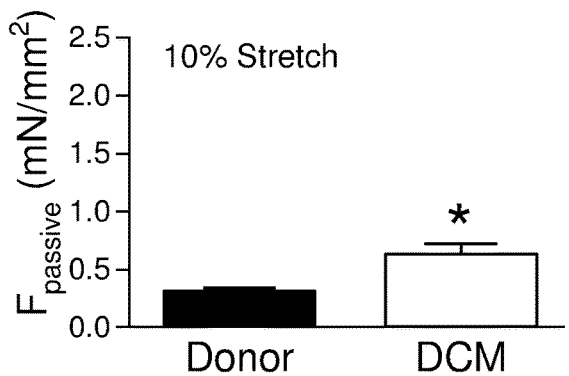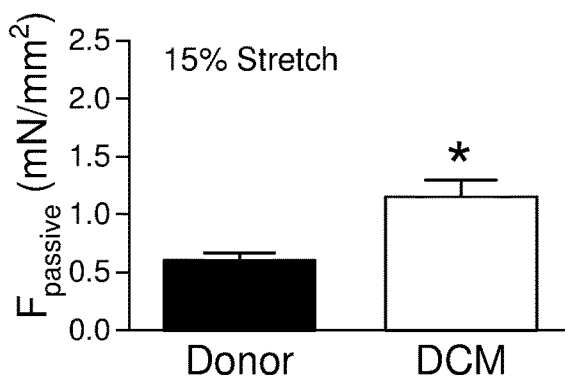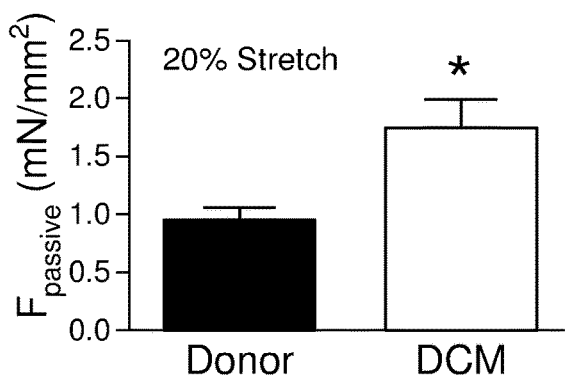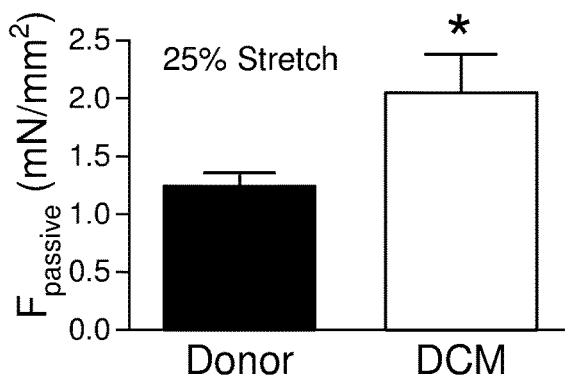
Fig. 3A    Fig. 3B

Fig. 7

```
  1 MDIAIHHPWI RRPFFPFHSP SRLFDQFFGE HLLESDLFPT STSLSPFYLR PPSFLRAPSW
 61 FDTGLSEMRL EKDRFSVNLD VKHFSPEELK VKVLGDVIEV HGKHEERQDE HGFISREFHR
121 KYRIPADVDP LTITSSLSSD GVLTVNGPRK QVSGPERTIP ITREEKPAVT AAPKK
```

SEQ ID NO.: 1

Fig. 8

```
  1 ATGGACATCG CCATCCACCA CCCCTGGATC CGCCGCCCCT TCTTTCCTTT CCACTCCCCC
 61 AGCCGCCTCT TGACCAGTT CTTCGGAGAG CACCTGTTGG AGTCTGATCT TTTCCCGACG
121 TCTACTTCCC TGAGTCCCTT CTACCTTCGG CCACCCTCCT TCCTGCGGGC ACCCAGCTGG
181 TTTGACACTG GACTCTCAGA GATGCGCCTG GAGAAGGACA GGTTCTCTGT CAACCTGGAT
241 GTGAAGCACT TCTCCCCAGA GGAACTCAAA GTTAAGGTGT TGGGAGATGT GATTGAGGTG
301 CATGGAAAAC ATGAAGAGCG CCAGGATGAA CATGGTTTCA TCTCCAGGGA GTTCCACAGG
361 AAATACCGGA TCCCAGCTGA TGTAGACCCT CTCACCATTA CTTCATCCCT GTCATCTGAT
421 GGGGTCCTCA CTGTGAATGG ACCAAGGAAA CAGGTCTCTG GCCCTGAGCG CACCATTCCC
481 ATCACCCGTG AAGAGAAGCC TGCTGTCACC GCAGCCCCCA AGAAATAG
```

SEQ ID NO.:2

Accession code NM_001289807.1

TREATMENT OF HEART FAILURE WITH PRESERVED EJECTION FRACTION

CROSS-REFERENCE TO RELATED APPLICATIONS

This application is a national phase entry under 35 U.S.C. § 371 of International Patent Application PCT/NL2017/050254, filed Apr. 21, 2017, designating the United States of America and published in English as International Patent Publication WO 2017/183978 A1 on Oct. 26, 2017, which claims the benefit under Article 8 of the Patent Cooperation Treaty to European Patent Application Serial No. 16166468.5, filed Apr. 21, 2016.

STATEMENT ACCORDING TO 37 C.F.R. § 1.821(c) or (e)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

TECHNICAL FIELD

The present disclosure, in general, relates to the field of medicine and particularly to medicaments and therapies for the treatment of diastolic heart failure (DHF) and diastolic dysfunction in a subject. More particularly, the present disclosure relates to the use of a protein encoded by a crystalline alpha B (CRYAB) gene in cardiomyocytes of the subject for treating diastolic dysfunction.

BACKGROUND

Diastolic dysfunction and diastolic heart failure (DHF) refers to the decline in performance of at least the left ventricle of the heart during diastole. Diastole is the cardiac cycle phase during which the heart is relaxing and filling with incoming blood that is being returned from the body. Diastolic dysfunction is considered a condition in which abnormalities in mechanical function of the heart, particularly in the functioning of the ventricles of the heart, are present during diastole. Abnormalities in diastolic function can occur in the presence or absence of a clinical syndrome of heart failure. Diastolic dysfunction appears when the left ventricle isn't filling properly during diastole because the ventricular wall can't relax or because the wall is too thick or rigid. Accordingly, any condition or process that leads to stiffening of the left ventricular wall can lead to diastolic dysfunction.

In failing hearts, diastolic dysfunction is mainly caused by stiff cardiomyocytes and interstitial collagen deposition. Cardiomyocytes or cardiac muscle cells (also known as myocardiocytes or cardiac myocytes) are the muscle cells that make up the cardiac muscle or heart. Each cardiomyocyte cell contains myofibrils arranged in sarcomeres, the fundamental contractile units of muscle cells. Sarcomeres are mainly composed of the protein myosin, which forms a thick filament, and the protein actin, which forms a thin filament, which long, fibrous filaments can slide past each in order to allow the cardiac muscle to contract or relax. In addition to myosin and actin, the giant cytoskeletal protein titin is an important protein in sarcomeres, which functions as a molecular spring that is responsible for the passive elasticity of the muscle. Titin binds to the thick filament (myosin) system, and provides binding sites for numerous proteins. Stiffening of the cardiomyocytes causing diastolic dysfunction is mainly due to altered elastic properties of titin in these cells. A subject may be determined to have diastolic heart failure if he has signs and symptoms of heart failure, a normal left ventricular ejection fraction and evidence of diastolic left ventricular dysfunction. Whether a subject suffers from diastolic dysfunction can, for instance, be determined by a Doppler echocardiographic examination of the subject.

DHF is a clinical syndrome characterized by an abnormal diastolic function (diastolic dysfunction) combined with symptoms and signs of heart failure and a preserved ejection fraction (EF) At present, there is no adequate therapy for DHF, or heart failure with preserved ejection fraction (HFPEF). In these forms of heart failure, contractile performance of the heart is relatively preserved but diastolic left ventricular (LV) function is greatly impaired with slow LV relaxation and high diastolic LV stiffness. No single therapy was so far able to improve diastolic LV dysfunction. The benefits of a therapy that specifically targets diastolic dysfunction and diastolic heart failure are apparent in view of diastolic LV dysfunction being the main cardiac disturbance in DHF and no single therapy has so far been shown to alter outcome or symptoms in large randomized trials targeting DHF. Currently, more than 50% of heart failure patients suffer from DHF and its prevalence relative to systolic heart failure continues to rise at a rate of 1% per year. A consensus statement on the diagnosis of heart failure with normal left ventricle ejection fraction is provided in Paulus et al. (2007), European Heart Journal; Vol. 28; pp 2539-2550.

Accordingly, the disclosure provides compositions that are useful for treating diastolic dysfunction and/or diastolic heart failure in a subject and, in particular, for use in treatment of diastolic dysfunction in a subject caused by stiffening of the cardiomyocytes in the heart of the subject.

BRIEF SUMMARY

The disclosure provides compositions for use in treatment of diastolic dysfunction and DHF. In particular, the disclosure provides compositions for treating diastolic dysfunction and DHF caused by stiffening of cardiomyocytes in the heart of the subject. More particularly, the disclosure provides compositions for use in treatment of a subject with a failing heart demonstrating diastolic dysfunction. The compositions for use according to the disclosure are particularly capable of reducing or removing increased stiffness of cardiomyocytes in the heart of the subject. More particularly, the disclosure provides compositions for use in treatment of diastolic dysfunction and DHF, which compositions are capable of restoring the elastic properties of titin in cardiomyocytes of the subject. The compositions according to the disclosure may thus be used to treat subjects that have been determined to comprise stiffened cardiomyocytes, and/or have been shown to demonstrate diastolic dysfunction and/or have been diagnosed to suffer from DHF. In particular, subjects that have an amount of stiffened cardiomyocytes in the heart exceeding that of a generally healthy heart, i.e., a heart with a normal diastolic function, may be treated with the compositions for use according to the disclosure. Therefore, apart from subjects with DHF, subjects with other conditions such as aortic stenosis and/or dilated cardiomyopathy may also be treated with the compositions for use according to the disclosure.

Alpha-crystallin B chain, also referred to as α-B crystallin or crystallin alpha B, which is encoded by the CRYAB gene in humans, is part of the small heat shock protein family and functions as a molecular chaperone that primarily binds misfolded proteins to prevent protein aggregation, as well as inhibit apoptosis and contribute to intracellular architecture. External Ids are HGNC: 2389; Entrez Gene: 1410; Ensembl: ENSG00000109846; OMIM: 123590 and UniProtKB: P02511. Post-translational modifications decrease the ability of alpha-crystallin B chain to chaperone. Defects in CRYAB and alpha-crystallin B chain protein have been associated with cancer and neurodegenerative diseases such as Alzheimer's disease and Parkinson's disease. In the present disclosure, it was found that expression of alpha-crystallin B chain protein in cardiomyocytes of a subject affects the stiffness of the cardiomyocytes. In particular, it was found that an expression of alpha-crystallin B chain protein in cardiomyocytes of a subject with diastolic dysfunction affects an existing increase in stiffness of the cardiomyocytes. More particularly, an increase in activity or expression of alpha-crystallin B chain protein in cardiomyocytes of a subject with diastolic dysfunction reduces an existing increase in stiffness of the cardiomyocytes and treats diastolic dysfunction and DHF. The disclosure provides a composition for use in treatment of diastolic dysfunction and DHF, which composition comprises a therapeutically effective amount of a substance that increases an activity and/or expression of alpha-crystallin B chain protein in cardiomyocytes of a subject.

In a particular embodiment of the composition for use according to the disclosure, the substance increases an alpha-crystallin B chain protein level in cardiomyocytes of the subject. In one embodiment, the substance may comprise a therapeutically effective amount of a polypeptide having an amino acid sequence of SEQ ID NO:1 (FIG. 7) or an amino acid sequence that has an amino acid sequence identity of at least 80%, preferably at least 90%, more preferably at least 95%, most preferably 100% with the alpha-crystallin B chain protein of SEQ ID NO:1. Preferably, the polypeptide reduces a stiffness of cardiomyocytes in a heart of a subject. More preferably, the polypeptide restores the elastic properties of titin in cardiomyocytes of a subject with diastolic dysfunction.

In an alternative embodiment of the composition for use according to the disclosure, the substance provides for enhanced expression of the CRYAB gene or the substance provides a nucleic acid segment encoding a polypeptide that has an amino acid sequence identity of at least 80%, preferably at least 90%, more preferably at least 95%, most preferably 100% with the alpha-crystallin B chain protein of SEQ ID NO:1, and particularly having at most a two amino acids difference with the sequence of SEQ ID NO:1. The enhanced expression of the CRYAB gene or the nucleic acid supplements the naturally occurring expression of alpha-crystallin B chain, thereby increasing a total amount or level of the alpha-crystallin B chain protein or functionally equivalent polypeptide in the cell. The enhanced expression may comprise an ectopic expression of the CRYAB gene. Ectopic expression is referred to herein as the expression of a coding sequence in an abnormal place in an organism or from an abnormal chromosomal position in the cell, and/or a sequence coding for a heterologous protein that is not normally expressed in the cell. Ectopic expression is typically achieved by artificially introducing a nucleic acid that codes for the respective expressed nucleic acid in the cell. Ectopic expression of a nucleic acid can be done by introducing a transgene with a (modified) promoter into the target cell (transient or stable transfection).

In a particular embodiment, the substance in the composition for use according to the disclosure increases an alpha-crystallin B chain protein level by enhancing expression of the CRYAB gene in cardiomyocytes of the subject. The substance can, for instance, comprise a small molecule or small RNA that is capable of increasing CRYAB gene expression in cells of the subject, such as, for instance, by activating a transcription factor. The substance may alternatively or in addition to such a small molecule or small RNA also comprise one or more other gene regulation peptides that promote gene transcription, such as, for example, a coactivator, chromatin remodeler, histone acetylase, kinase, and methylase. Geranyl-geranyl acetone (hereinafter referred to as GGA) has been reported to induce expression of heat shock proteins. GGA is manufactured by Eisai Co., Ltd. under the product name "Selbex." GGA has the generic name of teprenone, and is widely used as a drug to treat stomach ulcers and stomach inflammation. GGA may be acquired as a reagent or industrial raw material. It can be synthesized using well-known methods of synthesis. The chemical name of GGA is 6, 10, 14, 18-tetramethyl-5, 9, 13, 17-nonadecatetraen-2-one. GGA, or a derivative thereof, particularly the derivative NYK9354, is capable of inducing expression of CRYAB in cardiomyocytes. Administration of an effective amount of GGA or a derivative thereof such as NYK9354 results in higher expression levels of alpha B-crystallin protein in cardiomycocytes. Suitable derivatives and the synthesis thereof are described in U.S. Pat. No. 4,169,157, which is incorporated by reference herein for the suitable derivatives and their method of synthesis.

GGA is a registered drug and as such used in clinical trials and a clinical setting. The total amount of GGA administered over a fourteen-hour period can be, for example, 10-1,000 mg, e.g., 50-500 mg, e.g., 100-300 mg, as determined to be appropriate by those of skill in this art. The amount of GGA administered can vary, depending on the body weight of the patient and/or the tolerance of the patient. The disclosure also includes the use of GGA in the preparation of medicaments for preventing and treating the diseases and conditions described herein. In the context of the present disclosure, GGA can be given to individuals at a dose of between 1 mg-1 gram per day. The drug is preferably administered 3 times a day. Suitable dosage form comprises between 0.33 mg-1 gram GGA. The dosage form preferably comprises 1-300 mg GGA, preferably 3-100 mg, more preferably 20-80 mg GGA. Clinical trials with GGA are described among others in Hongo et al. (2012), J. of Gastroenterology and hepatology; Volume 27; Pages 62-68; at clinicaltrials.gov in a study entitled "Efficacy and Safety of Teprenone in Patients With Acute Gastritis, Acute Gastric Lesion of Chronic Gastritis With Acute Exacerbation or Gastric Ulcer"; and a study entitled "The purpose of this study is to evaluate the efficacy of teprenone on chronic non-atrophic erosive gastritis and its therapeutic mechanism." The dosage form is typically an oral dosage form.

The enhanced expression of the CRYAB gene in cardiomyocytes of a subject with diastolic dysfunction reduces an existing cardiomyocytes stiffness and, therefore, is a suitable therapeutic method for treating diastolic dysfunction and the symptoms affiliated therewith in diastolic heart failure. In a particular embodiment according to the present disclosure, the substance in the composition for use comprises GGA or a derivative thereof, particularly NYK9354.

The composition for use according to the disclosure in an alternative embodiment comprises a substance that increases the alpha-crystallin B chain protein activity, for instance, a substance that affects a post-translational modification of alpha-crystallin B chain protein in cardiomyocytes of the subject. In a preferred embodiment hereof, the composition for use according to the disclosure comprises a substance that mediates a post-translational modification of alpha-crystallin B chain protein to increase the ability of alpha-crystallin B chain to chaperone.

Although one of the substances described in the foregoing may be used in a composition for use according to the disclosure for treating diastolic dysfunction and DHF, it is also envisaged that any combination of two or more of such substances are used in the composition for use according to the disclosure. Accordingly, in an embodiment, the composition for use in treating diastolic dysfunction in a subject comprises one or more of the foregoing substances that increase a level of alpha B-crystallin protein in muscle cells, particularly in cardiomyocytes. For instance, a composition comprising both an amount of a polypeptide that has an amino acid sequence identity of at least 80%, preferably at least 90%, more preferably at least 95%, most preferably 100% with the alpha B-crystallin protein, as well as an effective amount of GGA to induce expression of the CRYAB gene in cardiomyocytes of the subject to further increase an expression level of alpha-crystallin B chain protein in the cardiomyocytes may be used in treating diastolic dysfunction in a subject. Any other suitable combination of two or more of the substances mentioned herein may be taken to prepare the composition for use according to the present disclosure.

The disclosure also provides methods of treating a diastolic dysfunction or DHF in a subject. The methods of the disclosure comprise administering to the subject an effective amount of a substance that increases the level and/or activity of alpha B-crystallin, where a used dose is effective to at least partly treat a diastolic dysfunction of the heart of the subject, particularly to reduce the symptoms of the diastolic dysfunction, more particularly to restore the diastolic function in the subject, preferably to a level comparable to an average heart generally considered healthy in respect to diastolic functioning thereof.

In a particular embodiment, the method of the disclosure comprises administering to a subject demonstrating diastolic dysfunction, an effective amount of alpha B-crystallin protein.

Unless otherwise defined, all technical and scientific terms used herein have the same meaning as commonly understood by one of ordinary skill in the art to which this disclosure belongs. Methods and materials are described herein for use in the present disclosure. However, other suitable methods and materials known in the art can also be used. The materials, methods, and examples are illustrative only and not intended to be limiting, unless so indicated. The following definitions are used unless otherwise described.

Where herein mention is made of an alpha-crystallin B chain protein, it is preferred that the protein comprises the amino acid sequence of SEQ ID NO:1, or an amino acid sequence having an amino acid sequence identity of at least 80%, preferably at least 90%, more preferably at least 95%, most preferably 100% with the amino acid sequence of SEQ ID NO:1. In a preferred embodiment, the protein has at most a two amino acids difference with the amino acid sequence of SEQ ID NO:1. Alpha B chain crystalline protein is a protein of SEQ ID NO:1 or an orthologue thereof of another species, preferably another mammal alpha B chain crystalline protein that is also an amino acid sequence capable of reducing diastolic stiffness in cardiomyocyte cells of a subject that has a heart demonstrating diastolic dysfunction.

It is preferred that the protein affects a stiffness of cardiomyocytes of a subject with diastolic dysfunction. The protein preferably affects the elastic properties of titin in cardiomyocytes of the subject. Where herein mention is made to a CRYAB gene, reference is made to a nucleic acid that encodes a protein as defined in this paragraph. As used herein, the term "nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof.

In a preferred embodiment, the CRYAB gene comprises the coding region present in the sequence of SEQ ID NO:2 (FIG. 8). The reference may be to the gene as present on the chromosome of a human cell, i.e., including the promoter and transcription signals present thereon and including the introns. The reference also includes a cDNA of CRYAB. It typically refers to the coding region of CRYAB with or without one or more (artificial) introns, such as is typically used in nucleic acid molecules designed for directing heterologous expression of CRYAB.

The level of an alpha B chain crystalline protein is increased in a cell when the amount of alpha B chain crystalline protein in the cell is increased by at least 10%, preferably at least 20%, more preferably at least 30, 40, 50% or more when compared to the amount of alpha B chain crystalline protein in the cell prior to the increase. The activity of alpha B chain crystalline protein is increased in a cell when the activity of alpha B chain crystalline protein is increased by at least 10%, preferably at least 20%, more preferably at least 30, 40, 50% or more when compared to the activity of alpha B chain crystalline protein in the cell prior to the increase. Alpha B chain crystalline protein activity in a cell can be increased with or without a concomitant increase in the level of alpha B chain crystalline protein. A preferred but not limiting way of increasing the activity of alpha B chain crystalline protein in a cell is by administration of an effective amount of a substance that increases expression of a heat shock protein in the cell, such as geranylgeranylacetone (GGA) or NYK9354.

The CRYAB gene or the nucleic acid segment can be encoded by an expression cassette that is provided to the cell. Preferably, the expression cassette encodes an RNA transcript in which the coding region for the alpha-crystallin B chain protein is contained. Particularly, the expression cassette in addition to the sequence of interest, i.e., the CRYAB gene or the nucleic acid segment, contains additional sequences, for instance, a suitable promoter and a transcription termination sequence, for controlled and/or proper expression of the sequence of interest. It is within the skill of the artisan to design suitable expression cassettes and transcripts.

The expression cassette used is preferably a vector, preferably an expression vector. A vector typically comprises a DNA molecule used as a vehicle to artificially carry foreign genetic material into another cell, where it can be replicated and/or expressed. A vector containing foreign DNA is termed recombinant DNA. Some types of vectors are plasmids, viral vectors, cosmids, and artificial chromosomes.

In a particular embodiment according to the present disclosure, the substance comprises a vector that is suitable for transfecting or transducing cardiomyocytes of the subject and which vector carries at least one copy of a nucleic acid encoding CRYAB. In a preferred embodiment, the nucleic acid is a nucleic acid comprising the coding region of SEQ ID NO:2 or the nucleic acid segment. The number of copies of the gene or nucleic acid segments used may be adapted to an envisaged amount of alpha-crystallin B chain protein or functionally equivalent polypeptide to be expressed in the cells of the subject.

The expression vector is preferably suitable as a gene delivery vehicle to be introduced into the cell. Typically, the CRYAB gene or the nucleic acid segment is encoded by a viral or virus-based gene delivery vehicle. A preferred embodiment of the delivery vehicle is a viral vector such as an adenoviral vector and, more preferably, an adeno-associated virus vector. In a particular preferred embodiment, the substance in the composition according to the disclosure comprises an adeno-associated virus vector or a lentivirus vector, more particularly a lentivirus vector carrying the CRYAB gene. The disclosure thus also provides such expression vectors and delivery vehicles carrying the CRYAB gene or a nucleic acid segment encoding a polypeptide that has an amino acid sequence identity of at least 80%, preferably at least 90%, more preferably at least 95%, most preferably 100% with the alpha-crystallin B chain protein.

An expression cassette, vector or gene delivery vehicle such as a viral vector typically comprises all of the sequences that are required in cis to allow efficient transcription and translation of the coding region.

Polypeptides or polynucleotides can serve as the active ingredient in pharmaceutical compositions formulated for the treatment of the disorders as described above, i.e., diastolic dysfunction and/or diastolic heart failure. The active ingredient is present in a therapeutically effective amount, i.e., an amount sufficient when administered to substantially modulate the effect of the targeted protein or polypeptide to treat a disease or medical condition mediated thereby.

The term "therapeutically effective amount" as used herein refers to the quantity of the alpha B chain crystalline protein or nucleic acid according to the disclosure necessary to reduce or diminish an increased stiffening of cardiomyocytes. Amounts effective to achieve this goal will, of course, depend on the type and severity of the disease and the general condition, particularly the weight, of the patient.

The compositions can also include various other agents to enhance delivery and efficacy, e.g., to enhance delivery and stability of the active ingredients.

Thus, for example, the compositions can also include, depending on the formulation desired, pharmaceutically acceptable, non-toxic carriers or diluents, which are defined as vehicles commonly used to formulate pharmaceutical compositions for animal or human administration. The term "pharmaceutically acceptable carrier" as used herein refers to a carrier for administration of the active substance. The pharmaceutically acceptable carrier can comprise any substance or vehicle suitable for delivering the substance to a therapeutic target, such as muscle cells, in particular, heart muscle cells, more particularly cardiomyocytes of the subject. The term refers to any pharmaceutical carrier that may be administered without undue toxicity. Suitable carriers may be one or more optional stabilizers, diluents, or excipients.

The diluent is particularly selected so as not to affect the biological activity of the combination. Examples of such diluents are distilled water, buffered water, physiological saline, PBS, Ringer's solution, and dextrose solution. In addition, the pharmaceutical composition or formulation can include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant.

When the pharmaceutical composition includes a polypeptide as the active ingredient, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions, and lipids.

The pharmaceutical compositions can be administered for prophylactic and/or therapeutic treatments, particularly therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred.

The data obtained from cell culture and/or animal studies can be used in formulating a range of dosages for human subjects or patients. The dosage of the active ingredient typically lies within a range of circulating concentrations that include the ED50 with little or no toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, or intracranial method.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. For a desired color, taste, stability, buffering capacity, dispersion or other known desirable features, additional inactive ingredients may be added. Similar diluents can be used to make compressed tablets. Both tablets and capsules can be manufactured as sustained release products to provide for continuous release of medication over a period of time, e.g., over several hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane and nitrogen.

Figure 4A:
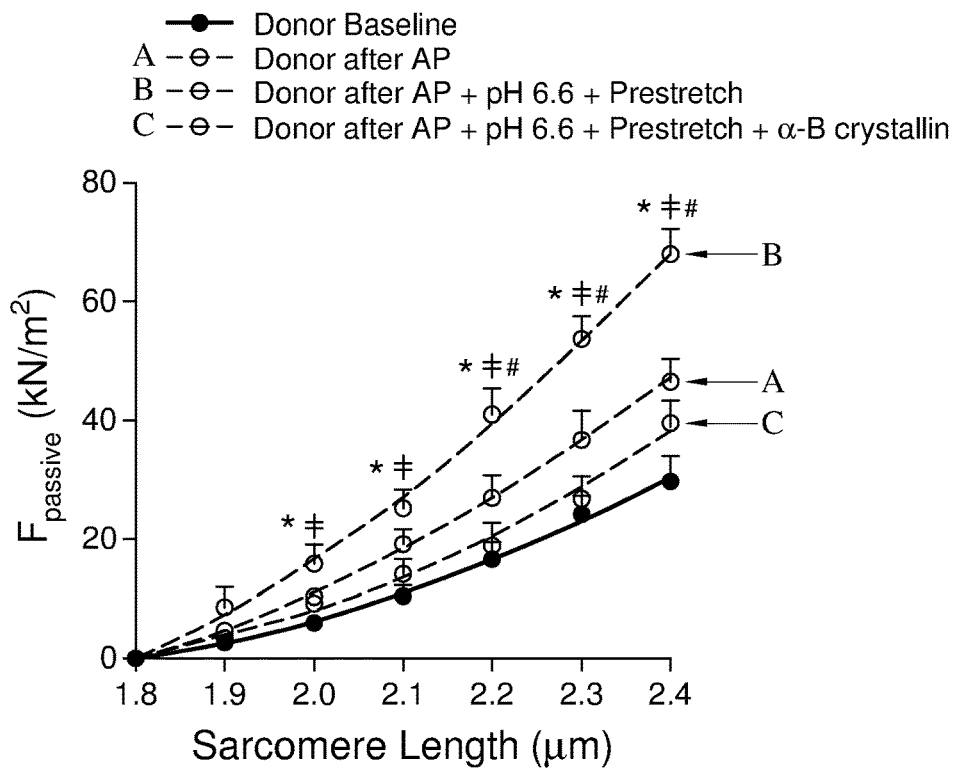
Figure 4B:
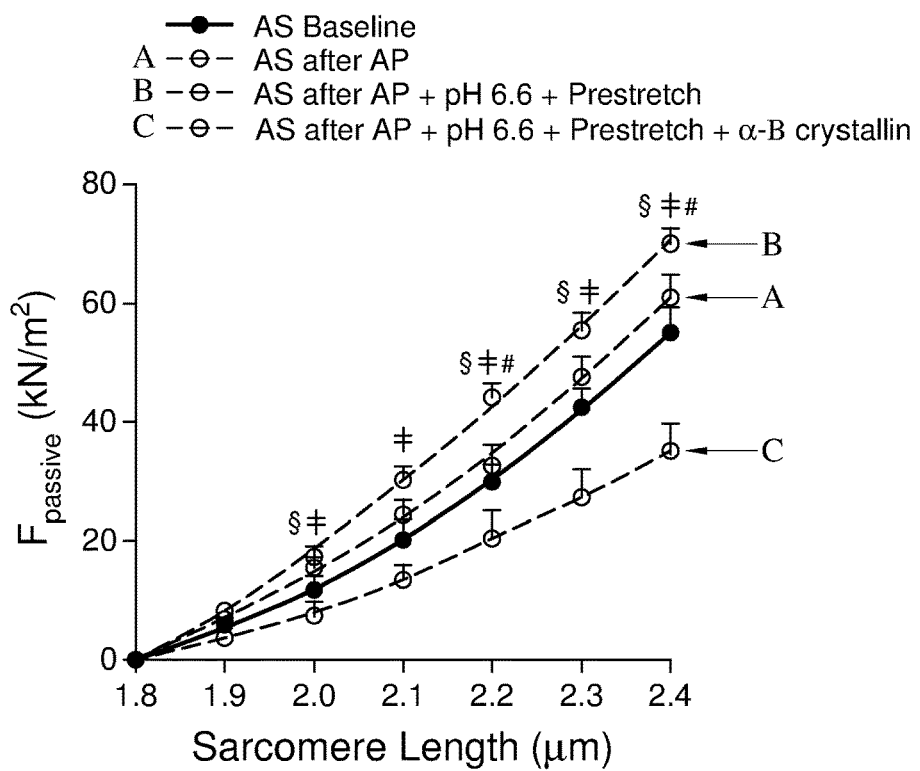
Figure 4C:
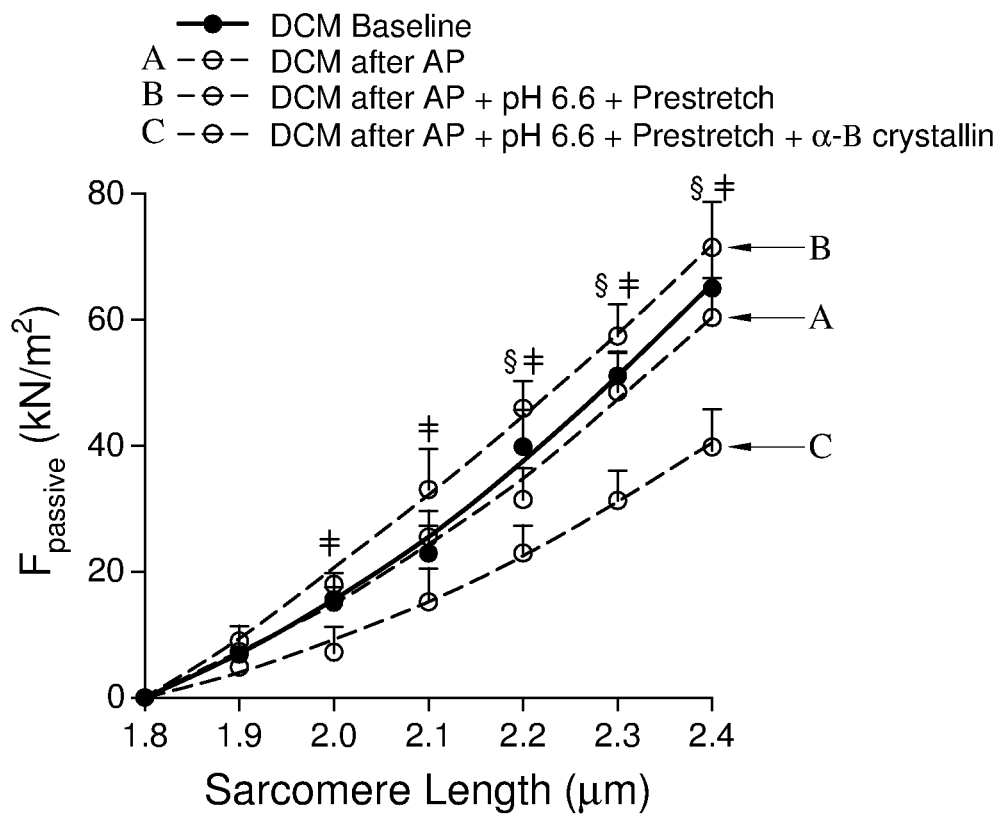

Formulations suitable for parenteral administration, such as, for example, by intravenous, intramuscular, intradermal, intraperitoneal, and subcutaneous routes, include aqueous and non-aqueous, isotonic sterile injection solutions, which can contain antioxidants, buffers, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are preferably sterile. To the extent that a given compound must be synthesized prior to use, the resulting product is preferably substantially free of any potentially toxic agents, such as any endotoxins, which may be present during the synthesis or purification process. Compositions for parental administration are also preferably sterile, substantially isotonic and made under GMP conditions.

The alpha-crystallin B chain compositions may be administered in a single dose, or in multiple doses, usually multiple doses over a period of time, e.g., daily, every-other day, weekly, semiweekly, monthly, etc., for a period of time sufficient to reduce severity of the disorder or disease, which may comprise 1, 2, 3, 4, 6, 10, or more doses.

Determining a therapeutically effective amount of an agent that provides alpha-crystallin B chain activity can be done based on animal data using routine computational methods. In one embodiment, the therapeutically effective amount contains between about 0.1 mg and about 1 g of nucleic acid or protein, as applicable. In another embodiment, the effective amount contains between about 1 mg and about 100 mg of nucleic acid or protein, as applicable. In a further embodiment, the effective amount contains between about 10 mg and about 50 mg of the nucleic acid or protein, as applicable. The effective dose will depend at least in part on the route of administration. The agents may be administered orally, in an aerosol spray, or by injection. The dose may be from about 0.1 μg/kg patient weight; about 1 μg/kg; about 10 μg/kg; to about 100 μg/kg.

The alpha-crystallin B chain compositions are administered in a pharmaceutically acceptable excipient. The term "pharmaceutically acceptable" refers to an excipient acceptable for use in the pharmaceutical and veterinary arts, which is not toxic or otherwise inacceptable. The concentration of alpha-crystallin B chain compositions of the disclosure in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

Treating, treatment, or therapy of a disease or disorder shall mean slowing, stopping or reversing the disease's progression by administration of an alpha-crystallin B chain composition. In the preferred embodiment, treating a disease means reversing the disease's progression, ideally to the point of eliminating the disease itself. Preventing, prophylaxis or prevention of a disease or disorder as used in the context of this disclosure refers to the administration of an alpha-crystallin B chain composition to prevent the occurrence or onset of a disease or disorder or some or all of the symptoms of a disease or disorder or to lessen the likelihood of the onset of a disease or disorder.

The term "dilated cardiomyopathy" or "DCM" as used herein shall mean the condition in a subject in which a portion of the myocardium, the left ventricle of the subject is dilated and left and/or right ventricular systolic pump function of the heart is impaired, leading to progressive cardiac enlargement and hypertrophy. DCM may be diagnosed in a subject when a generalized enlargement of the heart is seen upon normal chest X-ray and echocardiogram. The electrocardiogram often shows sinus tachycardia or atrial fibrillation, ventricular arrhythmias, left atrial enlargement, and sometimes intraventricular conduction defects and low voltage. Cardiac magnetic resonance imaging (cardiac MRI) may also provide helpful diagnostic information in patients with dilated cardiomyopathy.

The term "aortic stenosis" or "AS" as used herein shall mean the condition in a subject in which the exit of the left ventricle or aortic valve of the heart narrows such that problems, e.g., heart failure, occur. Aortic stenosis may be diagnosed by routine examination of the heart and confirmed by echocardiography. In particular, there may be a slow and/or sustained upstroke of the arterial pulse, and the pulse may be of low volume.

The term "subject" or "patient" as used herein shall mean any animal, such as a non-human primate, mouse, rat, guinea pig or rabbit, and particularly a human.

The disclosure will now be illustrated by means of the following figures and examples, which are provided by way of illustration and not of limitation. It will be understood that many variations in the methods described can be made without departing from the spirit of the disclosure and the scope of the appended claims. The drawings are not in any way meant to reflect a limitation of the scope of the disclosure, unless this is clearly and explicitly indicated.

BRIEF DESCRIPTION OF THE DRAWINGS

FIGS. 1A and 1B: $F_{passive}$ in myocardial strips. At baseline, $F_{passive}$ was significantly higher in dilated cardiomyopathy (DCM) strips and aortic stenosis (AS) strips compared to donor (FIG. 1A). After extracting thick and thin filaments, the remaining $F_{passive}$ can be attributed to the E-matrix and this was higher in DCM and AS than in donor (FIG. 1B). *P<0.05 DCM vs Donor; #P<0.05 AS vs Donor.

FIGS. 2A and 2B: $F_{passive}$ caused by the E-matrix. AS strips had significantly higher E-matrix based $F_{passive}$ than donor in stretches exceeding 15% from slack length (FIG. 2A). At all stages of muscle strain, $F_{passive}$ caused by the E-matrix was higher in DCM strips than in donor (FIG. 2B). #P<0.05 AS vs Donor; *P<0.05 DCM vs Donor.

FIGS. 3A and 3B: $F_{passive}$ caused by titin. In AS strips, titin-based $F_{passive}$ was higher than in donor strips at 10-20% stretches, but not at the highest stretches (FIG. 3A). At all stages of muscle strain, $F_{passive}$ caused by titin was higher in DCM strips than in donor (FIG. 3B). #P<0.05 AS vs Donor; *P<0.05 DCM vs Donor.

FIGS. 4A-4C: $F_{passive}$ in single myocytes. FIG. 4A: In donor cardiomyocytes, $F_{passive}$ significantly increased after administration of alkaline phosphatase and increased further after performing a prestretch in an acidic environment. After in vitro administration of α-B crystallin, $F_{passive}$ normalized again to baseline. FIG. 4B: In AS cardiomyocytes, no significant change in $F_{passive}$ was observed after incubation with alkaline phosphatases (AP). After the prestretch in pH 6.6, $F_{passive}$ increased significantly compared to baseline, but in vitro treatment with α-B crystallin dropped $F_{passive}$ to a level significantly lower than baseline. FIG. 4C: In DCM cardiomyocytes, incubation with AP had no effect on $F_{passive}$, but performing a prestretch in an acidic environment did increase passive stiffness significantly. After in vitro treatment with α-B crystallin, $F_{passive}$ dropped to a level significantly below baseline. *P<0.05 AP vs Baseline; #P<0.05 pH 6.6+Prestretch vs AP; ‡ P<0.05 α-B crystallin vs pH 6.6+Prestretch; § P<0.05 α-B crystallin vs Baseline.

Figure 5A:
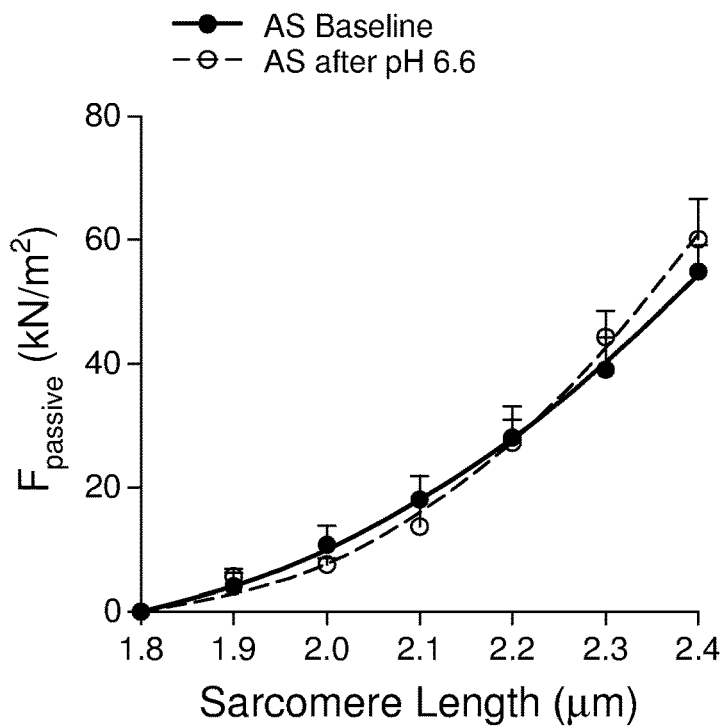
Figure 5B:
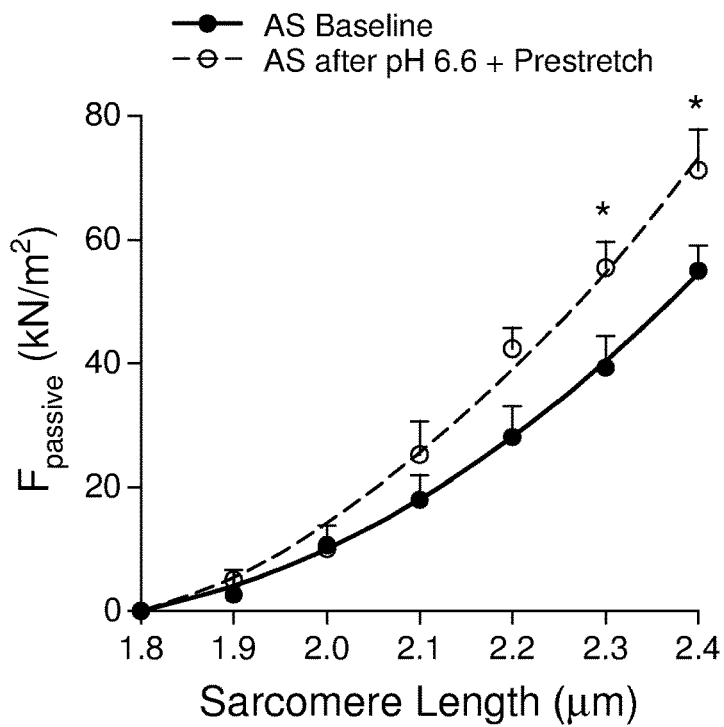

FIGS. 5A and 5B: Effects of Acidosis and Prestretch on Fpassive in single AS myocytes. Incubating single AS cardiomyocytes in pH 6.6 did not change $F_{passive}$ (FIG. 5A). Performing a prestretch to ~2.6 μm SL increased $F_{passive}$, but only significantly during higher stretches (FIG. 5B). *P<0.05 vs AS Baseline.

Figure 6A:
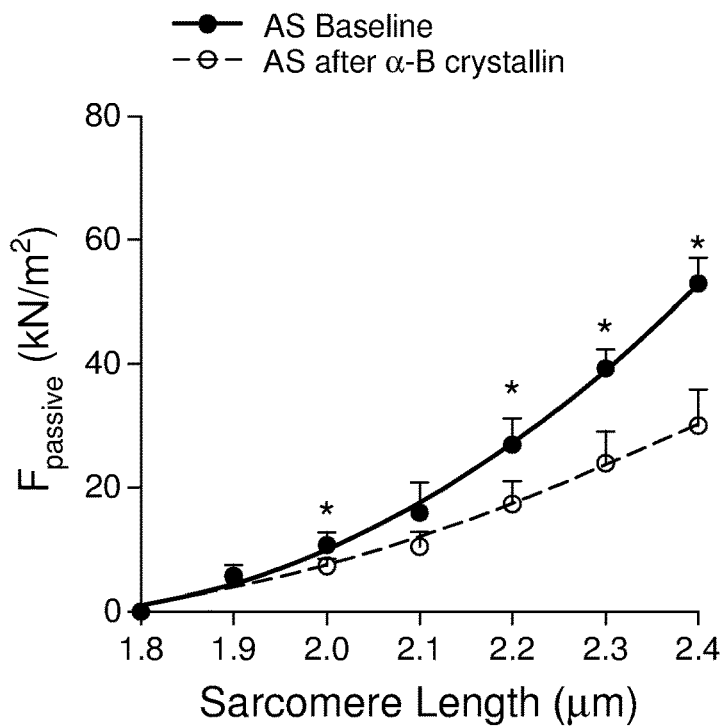
Figure 6B:
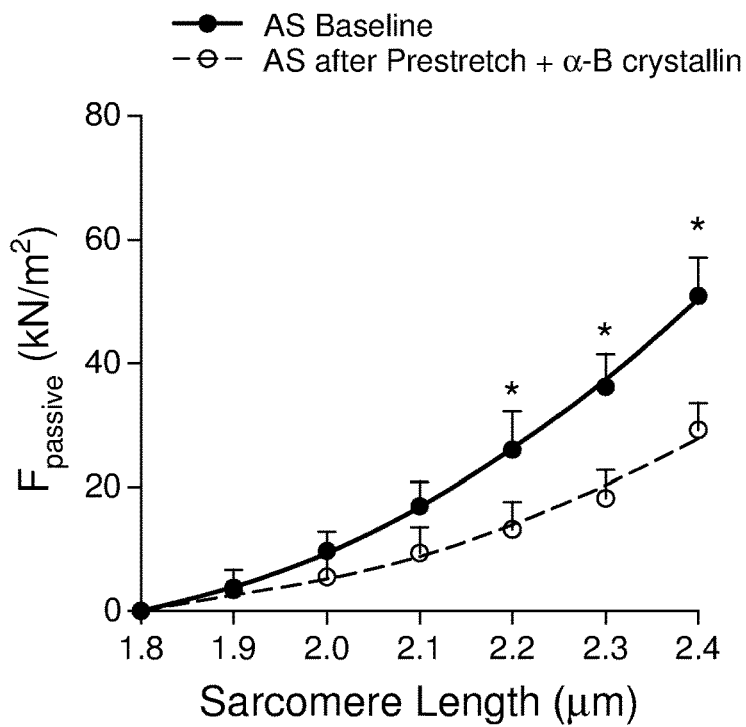
Figure 6C:
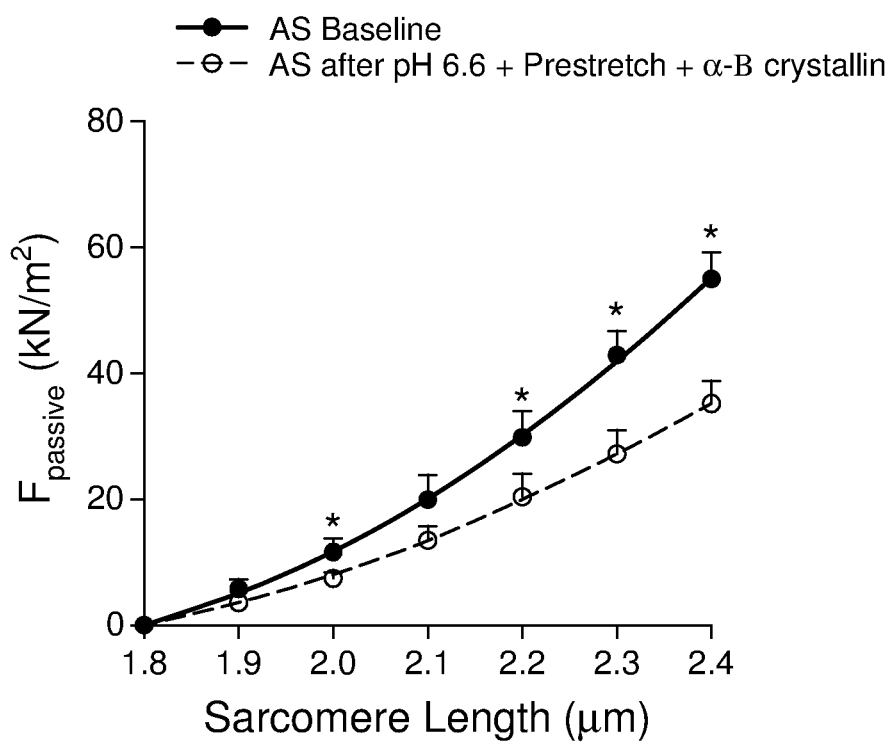

FIGS. 6A-6C: Effects of α-B crystallin at Baseline and after Acidosis and Prestretch on Fpassive in single AS cardiomyocytes. Incubation with α-B crystallin decreased $F_{passive}$ significantly (FIG. 6A). In single AS cardiomyocytes that underwent prestretch alone (FIG. 6B) or a prestretch in combination with pH 6.6 (FIG. 6C), α-B crystallin decreased $F_{passive}$ significantly as well. *P<0.05 vs AS Baseline.

FIG. 7: The amino acid sequence (SEQ ID NO:1) corresponding to a full length human alpha-crystallin B chain protein (CRYAB), natural variants of this protein exist.

FIG. 8: The nucleic acid sequence (SEQ ID NO:2) corresponding to a full length CRYAB cDNA of a human CRYAB.

Figure 9:
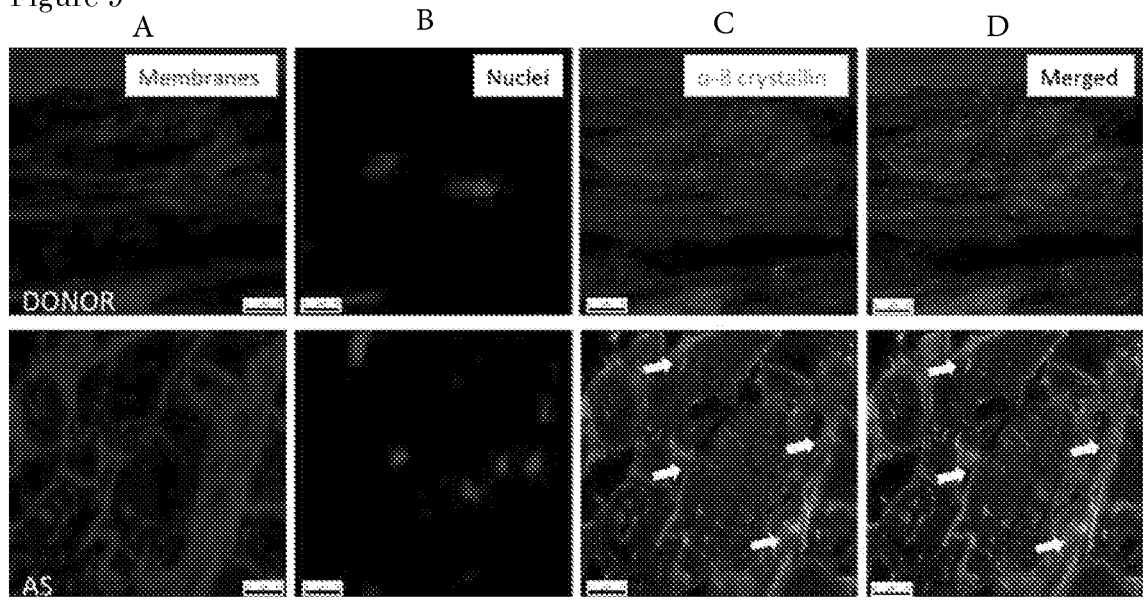

FIG. 9: Confocal laser microscopy for α-B crystallin in donor and aortic stenosis (AS). Confocal laser microscopic images were obtained from left ventricular (LV) myocardium of donor and AS patients with immunohistochemical visualization of cell membranes (Column A), nuclei (Column B), and α-B crystallin (Column C). In myocardium of AS patients, intensity of α-B crystallin expression (Column C) was higher than in donor with visualization in the merged images (Column D) of subsarcolemmal aggresomes especially in the vicinity of capillaries (white arrows). The latter suggests insufficient covering by α-B crystalline of sarcomeric proteins like titin in AS.

Figure 10:
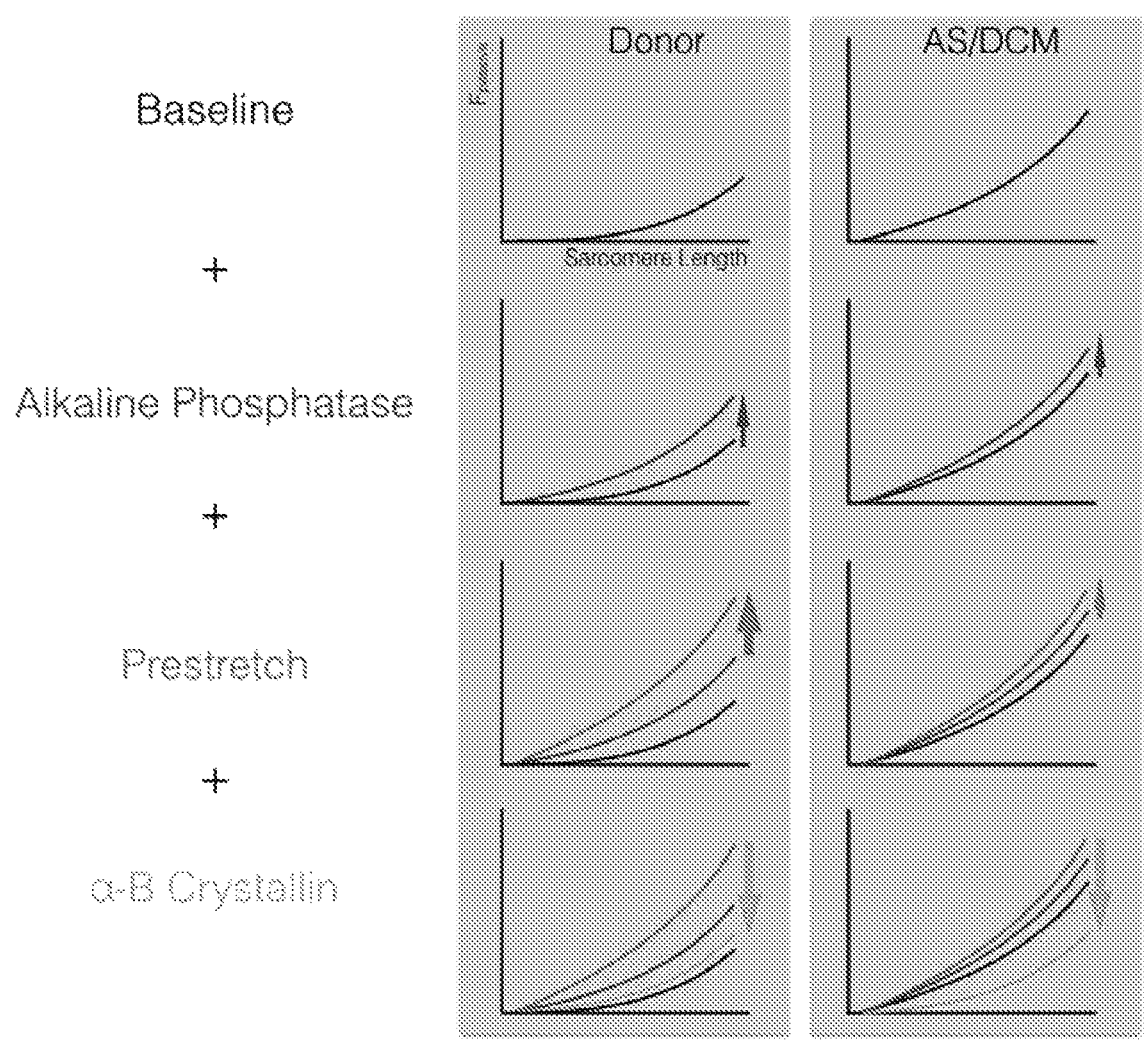

FIG. 10: Diagram showing respective responses of donor and aortic stenosis (AS)/dilated cardiomyopathy (DCM) cardiomyocytes to administration of alkaline phosphatase, prestretch, and α-B crystallin.

DETAILED DESCRIPTION

Human Samples

Aortic stenosis (AS) patients (N=7) had symptomatic, severe AS without concomitant coronary artery disease. Biopsy specimens from this group were procured from endomyocardial tissue resected from the septum (Morrow procedure) during aortic valve replacement. Dilated cardiomyopathy (DCM) specimens were procured from LV biopsies (N=3) or from explanted hearts from end-stage heart failure patients (N=3). DCM patients had no significant coronary stenosis and their biopsies showed no inflammation or infiltration. Control samples were obtained from explanted donor hearts (N=8).

Force Measurements in Small Muscle Strips

Small muscle strips (150-450 μm in diameter and 800-1900 μm in length) were dissected from biopsy specimens (n=24 for AS; n=16 for DCM; n=20 for Donor). After incubation for 1 hour in relaxing solution supplemented with 0.2% TritonX-100 to remove all membrane structures, strips were attached between a force transducer and length motor in a relaxing solution (in mmol/L: free Mg, 1; KCl, 100; EGTA, 2; Mg-ATP, 4; imidazole, 10; pH 7.0). Strips were gently stretched till slack length, i.e., the minimal length at which passive tension ($F_{passive}$) is being built up. As a test of cell viability, each muscle strip was transferred from relaxing to maximally activating solution (pCa4.5), at which isometric force developed. After stabilization for 5 minutes in relaxing solution, strips were stretched to 10, 15, 20 and 25% relative to slack length and $F_{passive}$ was measured at each stage of muscle strain. Subsequently, thick and thin filaments were extracted by immersing the preparation in relaxing solution containing 0.6 mol/L KCl (45 minutes at 20° C.) followed by relaxing solution containing 1.0 mol/L KI (45 minutes at 20° C.).[1-3] After the extraction procedure, the muscle bundles were stretched again and the $F_{passive}$ remaining after KCl/KI treatment was ascribed to the extracellular matrix (E-matrix). At each stage of muscle strain, $F_{passive}$ following extraction was subtracted from baseline value to yield $F_{passive}$ attributable to cardiomyocyte-stiffness, or titin.

Figure 1B:
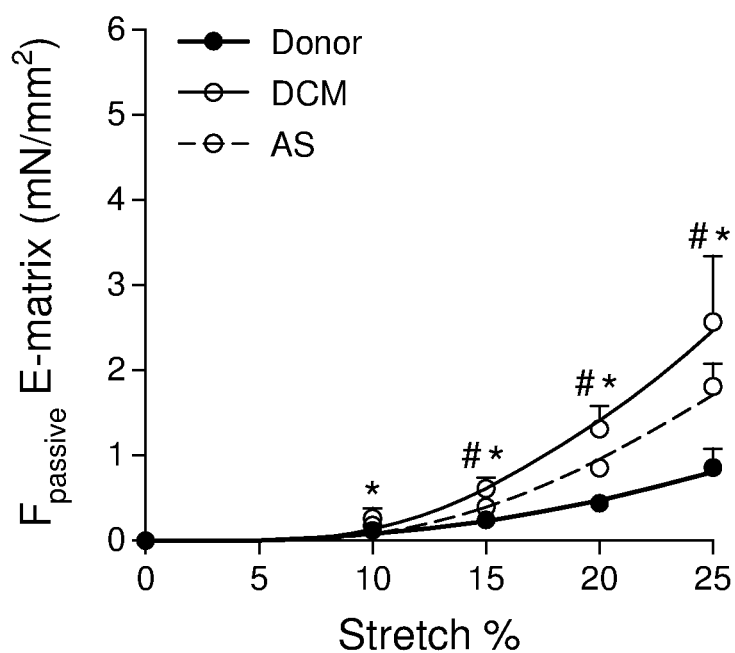

Initial stretches with intact muscle strips, in which both cardiomyocytes and E-matrix contribute to $F_{passive}$, showed that DCM and AS strips developed higher forces during all stretches compared to donors (FIG. 1A). The extraction protocol decreased $F_{passive}$ in all groups (FIG. 1B).

At all stages of muscle strain, $F_{passive}$ caused by the E-matrix was higher in DCM strips than in donors (FIG. 2B). AS strips had significantly higher E-matrix based $F_{passive}$ than donor in stretches exceeding 15% from slack length (FIG. 2A).

$F_{passive}$ related to cardiomyocyte stiffness, which is attributable to titin, was higher over the whole range of stretches in DCM and the range of stretches from 10-20% in AS (FIGS. 3A and 3B).

The difference in $F_{passive}$ related to titin cannot be explained by isoform shifts because both DCM and AS express more of the compliant N2BA titin isoform. To further analyze the difference in $F_{passive}$ related to titin, isolated cardiomyocytes were subjected to treatment with AP to discern the contribution of phosphorylation and to conditions prevailing in failing myocardium such as high stretch and hypoperfusion-related acidosis.

Force Measurements in Isolated Cardiomyocytes

Force measurements were performed on single demembranated cardiomyocytes (n ranged from 9 to 15 for each group and experimental protocol) as described previously.[4,5] Cardiomyocytes were isolated from donor, AS, and DCM hearts. Briefly, samples were thawed in relaxing solution (in mmol/L: free Mg, 1; KCl, 100; EGTA, 2; Mg-ATP, 4; imidazole, 10; pH 7.0), mechanically disrupted and incubated for 5 minutes in relaxing solution supplemented with 0.5% TRITON® X-100. The cell suspension was washed 5 times in relaxing solution. Single cardiomyocytes were selected under an inverted microscope and attached with silicone adhesive between a force transducer and a piezoelectric motor. Cardiomyocyte $F_{passive}$ was measured in relaxing buffer at room temperature within a sarcomere length (SL) range between 1.8 and 2.4 μm. Force values were normalized to cardiomyocyte cross-sectional area calculated from the diameter of the cells, assuming a cylindrical shape. As a test of cell viability, each cardiomyocyte was also transferred from relaxing to maximally activating solution (pCa4.5), at which isometric force developed. Once a steady state force was reached, the cell was shortened within 1 ms to 80% of its original length to determine baseline force. Only cells developing active forces >20 kN/m² were included in the analysis. Thereafter, cardiomyocytes were incubated in relaxing solution supplemented with alkaline phosphatases (AP) (2000 U/mL; New England Biolabs), 6 mmol/L dithiothreitol (MP Biochemicals) for 40 minutes at 20° C. and $F_{passive}$ was measured again at SL 1.8-2.4 μm. Subsequently, cardiomyocytes were stretched to ~2.6 μm SL, incubated in relaxing buffer with pH 6.6, and held in the stretched state for 15 minutes (prestretch). Thereafter, cardiomyocytes were returned to slack length and stabilized for 5 minutes before recording the $F_{passive}$ with an identical stretch protocol from SL 1.8-2.4 μm in the low pH buffer. Finally, the pH 6.6 buffer was supplemented with recombinant human α-B crystallin at 0.1 mg/ml and $F_{passive}$ was measured in the presence of α-B crystallin again at SL 1.8-2.4 μm.

In a second set of experiments, single AS cardiomyocytes underwent either incubation at pH 6.6 alone or a prestretch in relaxing buffer with pH 6.6 to ~2.6 μm SL, followed by the same stretch protocol from SL 1.8-2.4 μm.

Finally, in a third set of experiments, $F_{passive}$ was measured in single AS cardiomyocytes from SL 1.8-2.4 μm before and after incubation with α-B crystallin, before and after incubation with α-B crystallin and a prestretch to ~2.6 μm SL, and before and after incubation with α-B crystallin, a prestretch to ~2.6 μm SL and incubation at pH 6.6.

In donor cardiomyocytes (FIG. 4A), the $F_{passive}$-SL curve shifted upward after administration of alkaline phosphatase (AP), which dephosphorylates titin. In contrast, the $F_{passive}$-SL curve failed to shift in AS and DCM cardiomyocytes (FIGS. 4B and 4C), consistent with preexisting hypophosphorylation of titin. The $F_{passive}$-SL curve of donor cardiomyocytes after AP was still lower than the $F_{passive}$-SL curve after AP in AS and DCM cardiomyocytes. This suggests mechanisms other than hypophosphorylation to contribute to the high diastolic stiffness observed in AS and DCM cardiomyocytes. The additional effects of prestretch and acidic pH were, therefore, investigated. The $F_{passive}$-SL curve shifted further upward in donor cardiomyocytes after performing a prestretch and imposing an acidic pH. After administration of α-B crystallin, the curve returned to an intermediate position between baseline and AP.

In AS cardiomyocytes (FIG. 4B), no significant change in the $F_{passive}$-SL curve was observed after incubation with AP, consistent with a pre-existing hypophosphorylation of titin. After the prestretch and pH 6.6, the $F_{passive}$-SL curve shifted upward compared to baseline. After treatment with α-B crystallin, the $F_{passive}$-SL curve dropped to a position that was significantly lower than baseline and comparable to the baseline position of donor cardiomyocytes. This finding implies presence at baseline of prestretch- and pH-induced changes in AS myocardium, which could be corrected by administration of α-B crystallin.

The same series of experiments in single DCM cardiomyocytes show similar findings (FIG. 4C) as in AS cardiomyocytes: incubation with AP had no effect on the $F_{passive}$-SL curve, but performing a prestretch in an acidic environment shifted the curve significantly upward. After in vitro treatment with α-B crystallin, the $F_{passive}$-SL curve fell to a position that was significantly below baseline and comparable to the baseline position of donor cardiomyocytes. This again implies presence at baseline of prestretch- and pH-induced changes in DCM cardiomyocytes, which could be corrected by administration of α-B crystallin.

The relative importance of prestretch and pH 6.6 were analyzed in single AS cardiomyocytes. In the absence of prior administration of AP, lowering the pH to 6.6 had no effect on $F_{passive}$ (FIG. 5A), but a prestretch to ~2.6 μm SL significantly shifted the $F_{passive}$-SL curve upward (FIG. 5B).

Incubation with α-B crystallin shifted the $F_{passive}$-SL curve significantly downward compared to baseline (FIG. 6A). Prestretch or prestretch in combination with pH 6.6 yielded a similar result (FIGS. 6B and 6C). These findings suggest that prestretch-induced changes significantly contributed to the high stiffness of AS cardiomyocytes, both at baseline and after prestretch. The finding that high stiffness in the cardiomyocytes is reversed by addition of α-B crystallin suggests there is an insufficient availability of α-B crystalline in AS cardiomyocytes to neutralize stretch-induced effects on titin distensibility both at baseline and following prestretch. These results show that increasing the availability of alpha-crystallin B chain protein in cardiomyocytes that demonstrate a pre-existing stiffness is a means for lowering the stiffness of the cardiomyocytes, thereby forming a suitable treatment method for diastolic heart failure.

Immunofluorescence Staining and Confocal Scanning Laser Microscopy.

Frozen human heart tissue was sectioned to a thickness of 5 μm using a cryostat (Leica). The sections were fixed with 3% paraformaldehyde, permeabilized with 0.05% TWEEN® 20 and immunostained using goat anti-α-B crystallin (Santa Cruz) diluted 1 in 100 in PBS+1% BSA (immunohistochemical grade; Vector Laboratories). Anti-goat conjugated to Alexa 555 (Thermofisher) was used to visualize α-B crystallin. Membranes were stained using WGA conjugated with Alexa 647 (Thermofisher) diluted 1 in 100 in PBS. Nuclei were visualized using Picogreen reagent (Thermofisher) diluted 1 in 10 000 in PBS. Confocal scanning laser microscopy was performed on a Leica TCS SP8 STED 3X (Leica Microsystems). Picogreen, Alexa 555, and Alexa 647 were irradiated with a pulsed white light laser at 502, 553, and 631 nm, respectively. A 63× oil objective with NA 1.4 Numerical Aperture was used to image the sample. Detection of the fluorescent signal was performed with gated Hybrid Detectors. Finally, the images were deconvolved using Huygens Professional (Scientific Volume Imaging).

Scanning Laser Microscopy

Confocal laser microscopical images were obtained from LV myocardium of donor and AS patients with immunohistochemical visualization of cell membranes, nuclei, and α-B crystallin (FIG. 9). In myocardium of AS patients, intensity of α-B crystallin expression was higher than in donor with appearance of α-B crystallin-containing aggresomes18 (FIG. 9), which were especially prominent in the subsarcolemma close to the capillaries (white arrows in FIG. 9). The latter suggests signals originating from the microvascular endothelium to be involved in the subsarcolemmal mobilization of α-B crystallin in failing cardiomyocytes.

Statistical Analysis

Differences between groups were analyzed with an unpaired, two-tailed Student t test. Differences within groups were measured by repeated measures analysis of variance. All analyses were performed using Prism software (GraphPad Software Inc., version 6.0).

High diastolic stiffness of failing human myocardial strips and cardiomyocytes were investigated and the following was observed: (1) high diastolic stiffness of cardiomyocytes significantly contributes to the overall stiffness of LV myocardial strips of AS and DCM patients; (2) dephosphorylation with AP shifts the diastolic Fpassive-SL relation upward in donor but not in AS or DCM cardiomyocytes; (3) after dephosphorylation, exposure to prestretch causes an upward shift of the diastolic Fpassive-SL relations in AS and DCM cardiomyocytes and a further upward shift of the diastolic Fpassive-SL relation in donor cardiomyocytes; (4) subsequent administration of α-B crystallin shifts the diastolic Fpassive-SL relations downward in donor, AS, and DCM cardiomyocytes to a position that coincides with the baseline diastolic Fpassive-SL relation of donor cardiomyocytes and falls below the baseline diastolic Fpassive-SL relation in AS and DCM cardiomyocytes. This finding is consistent with α-B crystallin, providing protection against stretch-induced damage to titin in failing AS and DCM cardiomyocytes.

Cardiomyocyte Versus Extracellular Matrix Stiffness

High diastolic stiffness of failing human cardiomyocytes was a significant contributor to overall stiffness of LV myocardial strips of AS and DCM patients ≤20% stretch in AS and ≤25% stretch in DCM. Use of dissected myocardial strips precluded visualization of sarcomeres, and strip lengthening was, therefore, expressed as percentage of stretch with respect to slack length, that is, the minimal length at which Fpassive started to develop (FIGS. 1A and 1B). At 25% stretch, the contribution of cardiomyocyte stiffness to overall stiffness no longer differed between donor and AS cardiomyocytes but continued to differ between donor and DCM cardiomyocytes (FIGS. 3A and 3B). This could relate to less constraint by the extracellular matrix in DCM despite raised collagen volume fraction in both AS and DCM. The latter could be consistent with different distribution and homeostasis of myocardial fibrosis in AS and DCM: in DCM, there is focal replacement fibrosis, whereas in AS, there is diffuse reactive fibrosis and, as reflected by plasma biomarker elevations, fibrinolytic mechanisms are present in DCM in contrast to mainly profibrotic mechanisms in AS. These findings illustrate the importance of concentric versus eccentric remodeling for the constraint imposed by the extracellular matrix on the cardiomyocytes.

Cardiomyocyte Stiffness and Titin Dephosphorylation.

Altered cardiomyocyte stiffness can result from isoform shifts of the giant cytoskeletal protein titin, from post-translational modifications of titin such as phosphorylation, formation of disulfide bonds, carbonylation, and s-glutathionylation, or from stretch-induced titin modification. Because of higher expression of the compliant N2BA isoform in AS and DCM, titin isoform shifts do not contribute to the observed rise of cardiomyocyte stiffness observed in AS and DCM cardiomyocytes in the present disclosure. Because of altered activity in failing myocardium of different kinases such as protein kinase A, protein kinase C, protein kinase G, calcium/calmodulin-dependent kinase II, and extracellular signal regulated kinase, altered phosphorylation of titin by these kinases was suspected to be involved in the raised stiffness of failing human cardiomyocytes. The present disclosure observed treatment with AP to raise diastolic stiffness in donor cardiomyocytes but not in AS and DCM cardiomyocytes (FIG. 10). This implies a pre-existing imbalance of titin phosphorylation in AS and DCM cardiomyocytes with either reduced phosphorylation of sites that increase titin elasticity or increased phosphorylation of sites that decrease titin elasticity.

Post-translational modifications of titin other than phosphorylation have recently been implicated in altered cardiomyocyte stiffness. These mechanisms include, among others, modification of the titin molecule induced by excessive physical stretch. A previous study indeed showed stretch induced mechanical unfolding of immunoglobulin domains of titin to expose cryptic cysteines to S-glutathionylation, which interfered with the ability of titin to refold and left titin in a more extensible state. In acidic pH, the reverse was observed, namely, a prestretch-induced reduction of titin extensibility.[7] This is especially relevant to failing myocardium, which is exposed to both high filling pressures and jeopardized coronary perfusion. The present study, therefore, imposed prestretch and acidic pH on failing human cardiomyocytes.

Cardiomyocyte Stiffness and Prestretch

In the present study, cardiomyocytes were subjected to a prestretch protocol, which consisted of a 15-minute stretch period at 2.6 µm followed by a 5-minute stabilization period at slack length. This prestretch protocol was executed in Ph 6.6 in donor, AS, and DCM cardiomyocytes. After dephosphorylation with AP, exposure to prestretch caused an upward shift of the diastolic Fpassive-SL relations in AS and DCM cardiomyocytes and a further upward shift of the diastolic Fpassive-SL relation in donor cardiomyocytes (FIGS. 4A-4C). The identical position of all diastolic Fpassive-SL relations after prestretch argues in favor of previous stretch-induced damage being involved in the baseline elevation of diastolic stiffness of AS and DCM cardiomyocytes. The prestretch-induced upward shift of the diastolic Fpassive-SL relations in AS and DCM cardiomyocytes was indeed smaller than the prestretch induced upward shift of the diastolic Fpassive-SL relation in donor cardiomyocytes (FIG. 10). This yielded an identical position of all diastolic Fpassive-SL relations because in AS and DCM cardiomyocytes, a smaller shift was superimposed on baseline stretch-induced damage, whereas in donor cardiomyocytes, prestretch elicited a larger shift because of absent baseline stretch-induced damage.

Without being bound by theory, it is believed that the origin of the baseline stretch-induced damage in AS and DCM cardiomyocytes relates to external stretch on cardiomyocytes or to internal stretch within cardiomyocytes. The former relates to elevated LV filling pressures at rest or during exercise. The latter is consistent with either a modified Z-disc structure or with the previously observed widening of the Z-disc. Z-disc widening results from reduced elasticity of cytoskeletal proteins, which from both sides pull at and open up adjacent Z lines. In AS and DCM cardiomyocytes, internal stretch and stretch-induced damage could have resulted from the aforementioned imbalance of titin phosphorylation.

In contrast to a previous study, separate imposition of pH 6.6 failed to induce an upward shift of the diastolic Fpassive-SL relation (FIG. 5A). The upward shift of the diastolic Fpassive-SL relation after combined administration of prestretch and acidic pH, therefore, seemed to be solely related to preceding sarcomere stretch. Furthermore, omission of previous treatment with AP also did not influence the combined effect of prestretch and acidic pH (FIG. 5B).

Cardiomyocyte Stiffness and α-B Crystallin

α-B crystallin protects cardiomyocytes against stretch-induced damage in acidic pH (FIGS. 4A-4C). The present disclosure also administered α-B crystallin to AS and DCM cardiomyocytes. In contrast to donor cardiomyocytes, α-B crystallin not only corrected the combined effects of prestretch and acidic pH but also reversed the baseline upward displacement of the diastolic Fpassive-SL relation (FIG. 10). This finding was consistent with baseline involvement of previous stretch-induced titin damage in AS and DCM cardiomyocytes and was confirmed in a separate series of experiments, in which α-B crystallin shifted the diastolic Fpassive-SL relation downward without any previous or concomitant intervention (FIGS. 6A-6C). In these experiments, the magnitude of the downward displacement of the diastolic Fpassive-SL relation was similar in the absence (FIG. 6A) or presence of foregoing interventions (FIGS. 6B and 6C).

In AS and DCM cardiomyocytes, α-B crystallin lowered diastolic stiffness well below baseline values as previously reported after administration of protein kinase A or protein kinase G PKA or PKG. This supports overlapping effects of titin phosphorylation and stretch-induced titin aggregation possibly because of pre-existing stretch-induced titin aggregation obstructing phosphorylation at sites that specifically increase titin elasticity. This finding has important therapeutic implications as it implies limited efficacy of drugs that increase PKA or PKG activity for treatment of diastolic LV dysfunction related to high cardiomyocyte stiffness and could relate to the failure of dobutamine to improve diastolic LV dysfunction and of phosphodiesterase 5 inhibitors to improve exercise tolerance or hemodynamics in HFPEF.

The present disclosure observed upregulation and subsarcolemmal localization of α-B crystallin in AS and DCM cardiomyocytes. Because of the close vicinity of capillaries (white arrows in FIG. 7), the localization of α-B crystallin in subsarcolemmal aggresomes was consistent with signals from the microvascular endothelium being involved in their formation. The subsarcolemmal localization also suggested that endogenous α-B crystallin was diverted from the sarcomeres and, therefore, failed to exert its protective action on titin distensibility, which was, however, restored after administration of exogenous α-B crystallin. The latter finding supports future therapeutic efforts to raise concentration of α-B crystallin in failing myocardium through direct administration of α-B crystallin, through administration of α-B crystallin analogues or through administration of heat shock protein-inducing drugs such as geranylgeranylacetone or NYK9354.

High cardiomyocyte stiffness significantly contributed to overall myocardial stiffness in AS and DCM. High cardiomyocyte stiffness resulted from titin phosphorylation failing to improve cardiomyocyte stiffness and from previous stretch-induced aggregation of titin, both of which were corrected by administration of α-B crystallin. Diastolic LV dysfunction in heart failure could, therefore, benefit from treatment with α-B crystallin.

For the purpose of clarity and a concise description, features are described herein as part of the same or separate aspects and preferred embodiments thereof, however, it will be appreciated that the scope of the disclosure may include embodiments having combinations of all or some of the features described.

The following aspects are aspects of the disclosure:

Aspect 1. A composition for use in treatment of diastolic dysfunction in a subject, wherein the composition comprises a therapeutically effective amount of a substance that increases the level and/or activity of a crystalline protein in cardiomyocytes of the subject.

Aspect 2. Composition for use according to aspect 1, wherein the substance increases the level and/or activity of a crystalline protein that reduces a diastolic stiffness of the cardiomyocytes of the subject.

Aspect 3. Composition for use according to aspect 1 or aspect 2, wherein the crystalline protein that is increased in level and/or activity by the substance is a protein encoded by the crystalline alpha B (CRYAB) gene.

Aspect 4. Composition for use according to any one of the foregoing aspects, wherein the substance increases the level of alpha B chain crystalline protein in cardiomyocytes of the subject.

Aspect 5. Composition for use according to aspect 4, wherein the substance is alpha B chain crystalline protein of SEQ ID NO:1, or a protein that has an amino acid sequence identity of at least 80%, preferably at least 90%, more preferably at least 95%, most preferably 98% or 99% with the alpha B chain crystalline protein, which protein is capable of reducing a diastolic stiffness of cardiomyocytes of the subject.

Aspect 6. Composition for use according to aspect 4, wherein the substance induces expression of the CRYAB gene in the cardiomyocytes of the subject.

Aspect 7. Composition for use according to aspect 6, wherein the substance is geranylgeranylacetone (GGA) or NYK9354.

Aspect 8. Composition for use according to any one of aspect 1 to 3, wherein the substance mediates a post-translational modification of alpha B chain crystalline, preferably by phosphorylation of the alpha B chain crystalline protein.

Aspect 9. Composition for use according to any one of the foregoing aspects, wherein the subject to be treated suffers from diastolic heart failure or heart failure with preserved ejection fraction.

Aspect 10. Composition for use according to any one of the foregoing aspects, wherein the subject to be treated suffers from aortic stenosis and/or dilated cardiomyopathy.

Aspect 11. Method of treating diastolic dysfunction, diastolic heart failure or heart failure with preserved ejection fraction in a subject, comprising administering to the subject a therapeutically effective amount of a substance that increases the level and/or activity of a crystalline protein in cardiomyocytes of the subject.

REFERENCES

1. Granzier H. L., and T. C. Irving. Passive tension in cardiac muscle: contribution of collagen, titin, microtubules, and intermediate filaments. *Biophys. J.* 1995; 68(March): 1027-1044. doi: 10.1016/S0006-3495(95)80278-X.
2. Hamdani N., C. Franssen, A. Lourenco, et al. Myocardial titin hypophosphorylation importantly contributes to heart failure with preserved ejection fraction in a rat metabolic risk model. *Circ. Heart Fail.* 2013; 6(6):1239-49. doi: 10.1161/CIRCHEARTFAILURE.113.000539.
3. Zile M. R., C. F. Baicu, J. Ikonomidis, et al. Myocardial Stiffness in Patients with Heart Failure and a Preserved Ejection Fraction: Contributions of Collagen and Titin.; 2015. doi:10.1161/CIRCULATIONAHA.114.013215.
4. Borbély A., J. van der Velden, Z. Papp, et al. Cardiomyocyte stiffness in diastolic heart failure. *Circulation.* 2005; 111(6):774-81. doi:10.1161/01.CIR.0000155257.33485.6D.
5. Van Heerebeek L., A. Borbély, H. W. M. Niessen, et al. Myocardial structure and function differ in systolic and diastolic heart failure. *Circulation.* 2006; 113(16):1966-73. doi:10.1161/CIRCULATIONAHA.105.587519.
6. Borbély A., I. Falcao-Pires, L. van Heerebeek, et al. Hypophosphorylation of the Stiff N2B titin isoform raises cardiomyocyte resting tension in failing human myocardium. *Circ. Res.* 2009; 104(6):780-6. doi:10.1161/CIRCRESAHA.108.193326.
7. Kötter S., A. Unger, N. Hamdani, et al. Human myocytes are protected from titin aggregation-induced stiffening by small heat shock proteins. *J. Cell. Biol.* 2014; 204(2):187-202. doi:10.1083/jcb.201306077.

The invention claimed is:

1. A method of treating a subject for heart failure with preserved ejection fraction (HFpEF) characterized by diastolic dysfunction caused by diastolic stiffness of cardiomyocytes and interstitial collagen deposition, the method comprising:

administering to the subject a therapeutically effective amount of a substance that increases the level and/or activity of a crystalline protein in cardiomyocytes of the subject, wherein the substance is geranylgeranylacetone (GGA) or NYK9354.

2. The method according to claim 1, wherein the crystalline protein is alpha B-crystallin.

3. The method according to claim 2, wherein the therapeutically effective amount further reduces diastolic stiffness of cardiomyocytes in the subject.

4. A method for treating a subject for heart failure with preserved ejection fraction (HFpEF) characterized by diastolic dysfunction caused by diastolic stiffness of cardiomyocytes and interstitial collagen deposition, or for aortic stenosis, or is at risk of developing said heart failure or said aortic stenosis, the method comprising:
   administering to the subject a composition comprising a therapeutically effective amount of a substance that increases the level and/or activity of a crystalline protein in the subject's cardiomyocytes,
   wherein the substance is geranylgeranylacetone (GGA) or NYK9354.

5. The method according to claim 4, wherein the crystalline protein is a protein encoded by the crystallin alpha B (CRYAB) gene.

6. The method according to claim 5, wherein the substance mediates a post-translational modification of alpha-crystallin B chain.

7. The method according to claim 6, wherein the substance mediates the post-translational modification of alpha-crystallin B chain by phosphorylation of alpha-crystallin B chain.

8. The method according to claim 4, wherein the substance increases the level of alpha-crystallin B chain in cardiomyocytes of the subject.

9. The method according to claim 8, wherein the substance induces expression of the CRYAB gene in the cardiomyocytes of the subject.

10. The method according to claim 4, wherein the substance mediates a post-translational modification of alpha-crystallin B chain.

11. The method according to claim 10, wherein the substance mediates the post-translational modification of alpha-crystallin B chain by phosphorylation of alpha-crystallin B chain.

* * * * *

SEQUENCE LISTING

<160> NUMBER OF SEQ ID NOS: 2

<210> SEQ ID NO 1
<211> LENGTH: 175
<212> TYPE: PRT
<213> ORGANISM: Homo sapiens

<400> SEQUENCE: 1

Met Asp Ile Ala Ile His His Pro Trp Ile Arg Arg Pro Phe Phe Pro
1               5                   10                  15

Phe His Ser Pro Ser Arg Leu Phe Asp Gln Phe Phe Gly Glu His Leu
            20                  25                  30

Leu Glu Ser Asp Leu Phe Pro Thr Ser Thr Ser Leu Ser Pro Phe Tyr
        35                  40                  45

Leu Arg Pro Pro Ser Phe Leu Arg Ala Pro Ser Trp Phe Asp Thr Gly
    50                  55                  60

Leu Ser Glu Met Arg Leu Glu Lys Asp Arg Phe Ser Val Asn Leu Asp
65                  70                  75                  80

Val Lys His Phe Ser Pro Glu Glu Leu Lys Val Lys Val Leu Gly Asp
                85                  90                  95

Val Ile Glu Val His Gly Lys His Glu Glu Arg Gln Asp Glu His Gly
            100                 105                 110

Phe Ile Ser Arg Glu Phe His Arg Lys Tyr Arg Ile Pro Ala Asp Val
        115                 120                 125

Asp Pro Leu Thr Ile Thr Ser Ser Leu Ser Ser Asp Gly Val Leu Thr
    130                 135                 140

Val Asn Gly Pro Arg Lys Gln Val Ser Gly Pro Glu Arg Thr Ile Pro
145                 150                 155                 160

Ile Thr Arg Glu Glu Lys Pro Ala Val Thr Ala Ala Pro Lys Lys
                165                 170                 175

<210> SEQ ID NO 2
<211> LENGTH: 528
<212> TYPE: DNA
<213> ORGANISM: Homo sapiens

<400> SEQUENCE: 2
atggacatcg ccatccacca ccctggatc cgccgcccct tctttccttt ccactccccc      60
agccgcctct tgaccagtt cttcggagag cacctgttgg agtctgatct tttcccgacg     120
tctacttccc tgagtccctt ctaccttcgg ccaccctcct tcctgcgggc acccagctgg    180
tttgacactg gactctcaga gatgcgcctg gagaaggaca ggttctctgt caacctggat    240
gtgaagcact tctccccaga ggaactcaaa gttaaggtgt gggagatgt gattgaggtg     300 catggaaaac atgaagagcg ccaggatgaa catggtttca tctccaggga gttccacagg    360
aaataccgga tcccagctga tgtagaccct ctcaccatta cttcatccct gtcatctgat    420
ggggtcctca ctgtgaatgg accaaggaaa caggtctctg gccctgagcg caccattccc    480
atcacccgtg aagagaagcc tgctgtcacc gcagccccca agaaatag                528